US009662384B2

(12) United States Patent
Dominowski et al.

(10) Patent No.: US 9,662,384 B2
(45) Date of Patent: May 30, 2017

(54) CATTLE REPRODUCTIVE DISEASE VACCINES

(75) Inventors: Paul Joseph Dominowski, Kalamazoo, MI (US); Michael John Huether, Lincoln, NE (US); Mark D. Goodyear, Lincoln, NE (US)

(73) Assignee: Zoetis Services LLC, Parsippany, NJ (US)

( * ) Notice: Subject to any disclaimer, the term of this patent is extended or adjusted under 35 U.S.C. 154(b) by 1173 days.

(21) Appl. No.: 12/820,566

(22) Filed: Jun. 22, 2010

(65) Prior Publication Data

US 2010/0266629 A1 Oct. 21, 2010

Related U.S. Application Data

(62) Division of application No. 10/647,919, filed on Aug. 26, 2003, now abandoned.

(60) Provisional application No. 60/405,969, filed on Aug. 26, 2002.

(51) Int. Cl.
| | |
|---|---|
| *A61K 39/295* | (2006.01) |
| *A61K 39/12* | (2006.01) |
| *A61K 39/245* | (2006.01) |
| *A61K 39/155* | (2006.01) |
| *A61K 39/02* | (2006.01) |
| *A61K 39/39* | (2006.01) |
| *C07K 14/005* | (2006.01) |
| *A61K 39/00* | (2006.01) |

(52) U.S. Cl.
CPC ........ *A61K 39/295* (2013.01); *A61K 39/0225* (2013.01); *A61K 39/39* (2013.01); *C07K 14/005* (2013.01); *A61K 39/00* (2013.01); A61K 2039/5252 (2013.01); A61K 2039/5254 (2013.01); C12N 2710/16722 (2013.01); C12N 2720/10022 (2013.01); C12N 2760/18522 (2013.01); C12N 2760/18622 (2013.01); C12N 2770/24322 (2013.01); C12N 2770/28022 (2013.01)

(58) Field of Classification Search
None
See application file for complete search history.

(56) References Cited

U.S. PATENT DOCUMENTS

| | | | |
|---|---|---|---|
| 3,634,587 A | 1/1972 | Ament et al. | |
| 5,026,546 A | 6/1991 | Hilgers et al. | |
| 5,733,555 A | 3/1998 | Chu | |
| 6,291,228 B1 | 9/2001 | Howard et al. | |
| 6,436,410 B1 | 8/2002 | Krishnan et al. | |
| 6,787,146 B2 * | 9/2004 | Brake et al. | 424/269.1 |
| 7,323,182 B2 | 1/2008 | Garcon et al. | |
| 2004/0081666 A1 | 4/2004 | Dominowski | |

OTHER PUBLICATIONS

Lidgate et al. Pharmaceutical Research (1989) 6 (No. 9): 748-752.*
Fulton et al., Antibody responses by cattle after vaccination with commercial viral vaccines containing bovine herpesvirus-1, bovine viral diarrhea virus, parainfluenza-3 virus, and bovine respiratory syncytial virus immunogens and subsequent revaccination at day 140, Vaccine, 1995, vol. 13, No. 8, pp. 725-733.*
Bowland, et al., Bovine respiratory disease: Commercial vaccines currently available in Canada, Canadian Veterinary Journal, Jan. 2000, vol. 41, No. 1, pp. 33-48.*
Coggins et al., "Attenuation of Virus Diarrhea Virus (Strain Oregon C24-V) for Vaccine Purposes", Veterinary Virus Research Institute, 539-545, (1961).
Kolar et al., "Use in Cattle of Formalin-Killed Polyvalent Vaccine with Adjuvant Against Infectious Bovine Rhinotracheitis, Bovine Viral Diarrhea, and Parainfluenza-3 Viruses", Am. J. Vet. Res., 33(7):1415-1420, (1972).
Fernelius et al., "Evaluation of β-Propiolactone-Inactivated-and Chloroform-Treated-Virus Vaccines Against Bovine Viral Diarrhea-Mucosal Disease", Am. J. Vet. Res., 33(7):1421-1431, (1972).
Phillips et al., "Evaluation of a Bovine Viral Diarrhea Vaccine Produced in a Porcine Kidney Cell Line", Am. J. Vet. Res., 36(2):135-140, (1975).
McClurkin et al., "Selected Isolates of Bovine Viral Diarrhea (BVD) Virus Propagated on Bovine Turbinate Cells: Virus Titer and Soluble Antigen Production as Factors in Immunogenicity of Killed BVD Virus", Archives of Virology, 58:119-125, (1978).
Lobmann et al., "Clinical Evaluation of a Temperature-Sensitive Bovine Viral Diarrhea Vaccine Strain", Am. J. Vet. Res., 45(12):2498-2503, (1984).
Lobmann et al., "Safety of a Temperature-Sensitive Vaccine Strain of Bovine Viral Diarrhea Virus in Pregnant Cows", Am. J. Vet. Res., 47(3):557-560, (1986).
Donis et al., "Differences in Virus-Induced Polypeptides in Cells Infected by Cytopathic and Noncytopathic Biotypes of Bovine Virus Diarrhea-Mucosal Disease Virus", Virology, 158:168-173, (1987).
Talens et al., "Efficacy of Viral Components of a Nonabortigenic Combination Vaccine for Prevention of Respiratory and Reproductive System Diseases in Cattle", JAVMA, 194(9):1273-1280, (1989).

(Continued)

*Primary Examiner* — Shanon A Foley
*Assistant Examiner* — Myron Hill
(74) *Attorney, Agent, or Firm* — Vyacheslav Vasilyev

(57) ABSTRACT

The present invention relates to combination vaccines and methods for treating or preventing diseases or disorders in an animal caused by infection by Bovine Viral Diarrhea Virus (BVDV) Types 1 and 2, Bovine Herpes Virus Type-1 (BHV-1), Bovine Respiratory Syncytial Virus (BRSV), Parainfluenza Virus (PI₃), *Campylobacter fetus, Leptospira canicola, Leptospira grippotyphosa, Leptospira hardj-prajitno, Leptospira icterohaemmorrhagiae, Leptospira hardjo-bovis* and *Leptospira pomona* by administering to the animal an effective amount of a combination vaccine. The combination vaccine can be a whole or partial cell inactivated or modified live preparation.

18 Claims, No Drawings

(56) References Cited

OTHER PUBLICATIONS

Corapi et al., "Characterization of a Panel of Monoclonal Antibodies and Their Use in the Study of the Antigenic Diversity of Bovine Viral Diarrhea Virus", Am. J. Vet. Res., 51(9):1388-1394, (1990).
Howard et al., "Immunity of Bovine Virus Diarrhoea Virus in Calves: The Role of Different T-Cell Subpopulations Analysed by Specific Depletion in Vivo with Monoclonal Antibodies", Veterinary Immunology and Immunopathology, 32:303-314, (1992).
Larsson et al., "Bovine Virus Diarrhoea Virus Induces In Vitro a Proliferative Response of Peripheral Blood Mononuclear Cells from Cattle Immunized by Infection", Veterinary Microbiology, 31:317-325, (1992).
Bolin, "Control of Bovine Viral Diarrhea Infection by Use of Vaccination", The Veterinary Clinics of North America: Food Animal Practice, 11(3):615-625, (1995).
Fulton et al., "Antibody Responses by Cattle after Vaccination with Commercial Viral Vaccines Containing Bovine Herpesvirus-1, Bovine Viral Diarrhea Virus, Parainfluenza-3 Virus, and Bovine Respiratory Syncytial Virus Immunogens and Subsequent Revaccination at Day 140", Vaccine, 13(8):725-733, (1995).
Cortese et al., "BVD Virus Transmission Following Attenuated Vaccines to BVDV Seronegative Cattle", Large Animal Practice, 18(5):18-24, (1997).
Lambot et al., "Characterization of the Immune Response of Cattle Against Non-Cytopathic and Cytopathic Biotypes of Bovine Viral Diarrhoea Virus", Journal of General Virology, 78:1041-1047, (1997).
Beer et al., "Cytotoxic T-Lymphocyte Responses in Cattle Infected with Bovine Viral Diarrhea Virus", Veterinary Micobiology, 58:9-22, (1997).
Flores et al., "Clinical, Pathological and Antigenic Aspects of Bovine Viral Diarrhea Virus (BVDV) Type 2 Isolates Identified in Brazil", Veterinary Microbiology, 77:175-183, (2000).
Beer et al., "A New Inactivated BVDV Genotype I and II Vaccine: An Immunisation and Challenge Study with BVDV Genotype I", Veterinary Micobiology, 77:195-208, (2000).
Fulton et al., "Bovine Viral Diarrhea Virus Types 1 and 2 Antibody Responses in Calves Receiving Modified Live Virus or Inactivated Vaccines", Vaccine, 19(2-3):264-274, (2001).

Anonymous: "Invest Early in CattleMaster 4 Vaccine to Get the Highest Rate of Return", Internet Article 1-2 (2002).
Package insert for BOVI-SHIELD™ 3.
Miller et al., "Infertility in Heifers Inoculated with Modified-Live Bovine Herpesvirus-1 Vaccinal Strains Against Infectious Bovine Rhinotracheitis on Postbreeding Day 14", American Journal of Veterinary Research, 50(4):551-554, (1989).
Yancey et al., "Recent Advances in Bovine Vaccine Technology", Journal of Dairy Science, 76:2418-2436 (1993).
Bowland et al., "Bovine Respiratory Disease: Commercial Vaccines Currently Available in Canada", Canadian Veterinary Journal, 41(1):33-48, (2000).
Barr et al., "ISCOMs and Other Saponin Based Adjuvants", Advanced Drug Delivery Reviews, 32:247-271, (1998).
Pruett et al., "Effects of Adjuvants on Bovine Humoral and Cellular Responses to Hypodermin A", Veterinary Parasitology, 58(12):143-163, (1995).
Willson et al., "Tissue Reaction and Immunity in Swine Immunized with Actinobacillus Pleuropneumoniae Vaccines", Canadian Journal of Veterinary Research, 59(4):299-305, (1995).
Copland et al., "Hydration of Lipid Films with an Aqueous Solution of Quil A: A Simple Method for the Preparation of Immune-Stimulating Complexes", International Journal of Pharmaceutics, 196:135-139, (2000).
Ficken et al., "Effects of Modified-Live Bovine Viral Diarrhea Virus Vaccines Containing Either Type 1 or Types 1 and 2 BVDV on Heifers and Their Offspring after Challenge with Noncytopathic Type 2 BVDV During Gestation", JAVMA, 228(10):1559-1564, (2006).
Howard et al., "Systemic Vaccination with Inactivated Bovine Virus Diarrhoea Virus Protects Against Respiratory Challenge", Veterinary Microbiology, 42:171-179, (1994).
Brownlie et al., "Protection of the Bovine Fetus from Bovine Viral Diarrhoea Virus by Means of a New Inactivated Vaccine", Veterinary Record, 137:58-62, (1995).
Cortese et al., "Protection of Pregnant Cattle and their Fetuses Against Infection with Bovine Viral Diarrhea Virus Type 1 by use of a Modified-Live Virus Vaccine", Am. J. Vet. Res., 59(11):1409-1413, (1998).
Cravens et al., "Efficacy of a temperature-sensitive modified live bovine herpesvirus type-1 vaccine against abortion and stillbirth in pregnant heifers", J. Am. Vet. Med. Assoc., 208(12):2031-2034, 1996.

* cited by examiner

CATTLE REPRODUCTIVE DISEASE VACCINES

CROSS REFERENCE TO RELATED APPLICATIONS

This application is a divisional application of U.S. patent application Ser. No. 10/647,919, filed Aug. 26, 2003, which is pending, and which claims benefit under 35 U.S.C. 119 of U.S. Provisional Patent Application Ser. No. 60/405,969, filed Aug. 26, 2002. The entire disclosures of both applications are incorporated herein by reference.

FIELD OF THE INVENTION

The present invention relates to combination vaccines and methods for treating or preventing diseases or disorders in an animal caused by infection by Bovine Viral Diarrhea Virus (BVDV) Types 1 and 2, Bovine Herpes virus Type-1 (BHV-1), Bovine Respiratory Syncytial Virus (BRSV), Parainfluenza Virus ($PI_3$), *Campylobacter fetus, Leptospira canicola, Leptospira grippotyphosa, Leptospira borgpetersenii hardjo-prajitno, Leptospira icterohaemmorrhagiae, Leptospira borgpetersenii hardjo-bovis* and *Leptospira interrogans pomona* by administering to the animal an effective amount of a combination vaccine. The combination vaccine can be a whole or partial cell inactivated or modified live preparation.

BACKGROUND OF THE INVENTION

Five viral agents associated with the bovine respiratory disease (BRD) complex—Bovine Herpes Virus Type-1 (BHV-1), also known as infectious bovine rhinotracheitis virus (IBR), Bovine viral diarrhea virus (BVDV) Types 1 and 2, Bovine Respiratory Syncytial Virus (BRSV), and Parainfluenza Virus ($PI_3$), cause respiratory and reproductive system infections of great economic importance to the cow-calf and dairy industries worldwide. BRD causes a broad array of clinical syndromes including acute onset respiratory disease and abortion. The respiratory form of BRD is characterized by inflammation, swelling, hemorrhage, and necrosis of the mucous membranes of the respiratory tract and may be accompanied by high fever, anorexia, depression, nasal discharge, labored breathing, and inflamed muzzle. Abortions induced by IBR and BVDV virus can occur in all three trimesters, but chiefly during the last half of gestation, and often without evidence of other clinical signs (Ellis et al. (1996) JAVMA 208:393-400; Ellsworth et al. (1994) In: Proceedings, 74th Conference of Research Workers in Animal Disease:34).

Bovine Herpes Virus Type-1 (BHV-1), is a member of the alphaherpesviridae subfamily, and produces a variety of clinical forms of disease in cattle, including respiratory and genital infections, conjunctivitis, encephalitis, and abortions. Previous attempts at controlling BHV-1 infection have utilized vaccines comprising live attenuated virus (Gerber, J. D., et al., 1978, Am. J. Vet. Res. 39:753-760; Mitchell, D., 1974, Can. Vet. Jour. 15:148-151), inactivated virus (Frerichs, G. N., et al., 1982, Vet. Rec. 111:116-122), and viral subunits such as, e.g., one of the three major BHV-1 glycoproteins, which have been designated in the art as gI, gIII, and gIV (Babiuk, L. A., et al., 1987, Virology 159:57-66; van Drunen, S., et al., 1993, Vaccine 11:25-35). In addition, the ability of a recombinant, truncated version of the BHV-1 gIV glycoprotein (designated in the art as BHV-1 tgIV) to induce mucosal immunity against BHV-1 has been demonstrated (van Drunen, S., et al., 1994, Vaccine, 12:1295-1302). However, the art-recognized BHV-1 vaccines are contraindicated for use in pregnant cattle, seropositive or seronegative, and also contraindicated for use in calves nursing pregnant cows.

BVDV Types 1 and 2 have been implicated in a variety of clinical syndromes. Studies have established that the virus causes severe primary respiratory disease; that persistently infected (PI) cattle are a major source of infection for susceptible calves; and that BVDV infects white cell reservoirs, causing profound and broad-based deficits in the immune system. Ellis et al. (1996) JAVMA 208:393-400; Baum et al. (1993) The Compendium Collection: Infectious Disease in Food Animal Practice. Trenton, N.J. Veterinary Learning Systems-113-121; Meyling et al. (1987) Agric Pestivirus Infect Rumin 225-231. Abortion or mummification can result when pregnant cattle become infected especially during the first trimester. Bolin et al. (1989) Am J. Vet Res 52:1033-1037. Mucosal disease, another often fatal manifestation of bovine viral diarrhea (BVD), results from early fetal infection with a noncytopathic BVDV biotype, development of immunotolerance to the virus, birth of a persistently infected (PI) calf, and subsequent superinfection with a cytopathic BVDV biotype. Bolin et al. (1989) Am J. Vet Res 52:1033-1037. BVDV Type 2, once recognized chiefly as a hemorrhagic BVDV isolate mostly in dairy herds, has become the predominant strain isolated in most regions of the United States from both BVD-related abortions and respiratory cases. Van Oirschot et al. (1999) Vet Micro 64:169-183.

BVDV is classified in the pestivirus genus and Flaviviridae family. It is closely related to viruses causing border disease in sheep and classical swine fever. Infected cattle exhibit "mucosal disease" which is characterized by elevated temperature, diarrhea, coughing and ulcerations of the alimentary mucosa (Olafson, et al., Cornell Vet. 36:205-213 (1946); Ramsey, et al., North Am. Vet. 34:629-633 (1953)). The BVD virus is capable of crossing the placenta of pregnant cattle and may result in the birth of PI calves (Malmquist, J. Am. Vet. Med. Assoc. 152:763-768 (1968); Ross, et al., J. Am. Vet. Med. Assoc. 188:618-619 (1986)). These calves are immunotolerant to the virus and persistently viremic for the rest of their lives. They provide a source for outbreaks of mucosal disease (Liess, et al., Dtsch. Tieraerztl. Wschr. 81:481-487 (1974) and are highly predisposed to infection with microorganisms causing diseases such as pneumonia or enteric disease (Barber, et al., Vet. Rec. 117:459-464 (1985).

According to BVDV virus growth studies in cultured cells, two viral biotypes have been classified: viruses that induce a cytopathic effect (cp) and viruses that do not induce a cytopathic effect (ncp) in infected cells (Lee et al., Am. J. Vet. Res. 18: 952-953; Gillespie et al., Cornell Vet. 50: 73-79, 1960). Cp variants can arise from the PI animals preinfected with ncp viruses (Howard et al., Vet. Microbiol. 13: 361-369, 1987; Corapi et al., J. Virol. 62: 2823-2827, 1988). Based on the genetic diversity of the 5' non-translated-region (NTR) and the antigenic differences in the virion surface glycoprotein E2 of BVD viruses, two major genotypes have been proposed: type I and II. BVDV type 1 represents classical or traditional virus strains which usually produce only mild diarrhea in immunocompetent animals, whereas BVDV type 2 are emerging viruses with high virulence which can produce thrombocytopenia, hemorrhages and acute fatal disease (Corapi et al., J. Virol. 63: 3934-3943; Bolin et al., Am. J. Vet. Res. 53: 2157-2163; Pellerin et al., Virology 203: 260-268, 1994; Ridpath et al., Virology 205: 66-74, 1994; Carman et al., J. Vet. Diagn. Invest. 10: 27-35, 1998). Type I and II BVDV viruses have distinct antigenicity determined by a panel of monoclonal antibodies (Mabs) and by cross-neutralization using virus-specific antisera raised in animals (Corapi et al., Am. J. Vet. Res. 51: 1388-1394, 1990). Viruses of either genotype may exist as one of the two biotypes, cp or ncp virus.

Studies from BVD virus infected animals suggest that BVD viruses induce both B-cell and T-cell responses in animals (Donis et al., Virology 158: 168-173, 1987; Larsson et al., Vet. Microbiol. 31: 317-325, 1992; Howard et al., Vet. Immunol. Immunopathol. 32: 303-314, 1992; Lambot et al., J. Gen. Virol. 78: 1041-1047, 1997; Beer et al., Vet. Microbiology. 58: 9-22, 1997).

A number of BVDV vaccines have been developed using chemically inactivated BVD viral isolates (Fernelius et al., Am. J. Vet. Res. 33: 1421-1431, 1972; Kolar et al., Am. J. Vet. Res. 33: 1415-1420, 1972; McClurkin et al., Arch. Virol. 58: 119, 1978). Multiple doses are required for the inactivated viral vaccines to achieve primary immunization. Some inactivated BVDV vaccines provide protection against infection by type I BVDV only (Beer et al., Vet. Microbiology. 77:195-208, 2000). Fetal protection has not been achieved with inactivated BVDV vaccines due to a short duration of immunity and an inefficient cross-type protection (Bolin, Vet. Clin. North Am. Food Anim. Pract. 11: 615-625, 1995).

Modified-live virus (MLV) vaccines, on the other hand, offer a higher level of protection. Currently, licensed BVDV MLV vaccines are produced using attenuated viruses obtained via repeated passage in bovine or porcine cells (Coggins et al., Cornell Vet. 51: 539-, 1961; Phillips et al., Am. J. Vet. Res. 36: 135-, 1975), or using chemically modifiedviruses which exhibit a temperature-sensitive phenotype (Lobmann et al., Am. J. Vet. Res. 45: 2498-, 1984; 47: 557-561, 1986). A single dose of MLV vaccine is sufficient for immunization, and duration of the immunity can last for years in vaccinated cattle. However, as these vaccines have been developed using type I BVDV virus strains, the protection is against type I virus only. Moreover, the available BVDV vaccines are not indicated for use in pregnant cattle or calves nursing pregnant cows.

$PI_3$ virus typically produces only mild disease when acting alone; however, the virus predisposes the respiratory tract to secondary infection with more pathogenic organisms including IBR virus, BRSV, and BVDV, resulting in the classic shipping fever syndrome. Of the various viruses known to cause respiratory disease in cattle, $PI_3$ virus is the most widespread. Ellis et al. (1996) JAVMA 208:393-400.

BRSV has a preference for the lower respiratory tract, and severity of infection is determined chiefly by the immune system's response to key viral proteins. Bolin et al. (1990) Am J Vet Res 51:703. Affected cattle generally show non-specific signs including serous nasal and ocular discharge, a mild, often biphasic fever, and dry, hacking cough. More severely affected cattle develop a harsh cough, show labored, open-mouth breathing, and frothy saliva around the mouth, and may quit eating and drinking. Ellis et al. (1996) JAVMA 208:393-400.

Leptospirosis, caused by spirochetes of the genus *Leptospira*, is an economically important zoonotic infection of livestock. *Leptospira borgpetersenii* serovar *hardjo* (*L. hardjo*) and *L. interrogans* serovar *pomona* (*L. pomona*) are the two serovars most commonly associated with cattle leptosporosis worldwide. In one survey of US cattle, 29% reacted serologically with *L. hardjo*, and 23% with *L. pomona*. Leptospires invade the body via mucous membranes or broken skin, and are disseminated via the blood. They display tropisms for the kidney and genital tract, and less commonly the vitreous humor of the eye and the central nervous system. The most common means of infection is by direct or indirect contact with infected urine, milk, or placental fluids, but venereal and trans-ovarian transmission are also known. Leptospiral infection of cattle may result in acute fever, agalactia, abortion, or birth of premature and weak infected calves, and may contribute to breeding failures and low conception rates. Infections can be treated with antibiotics, but they may be inapparent in cattle that are not lactating or pregnant. In such cattle they establish acute or chronic infection of the kidneys, resulting in urinary shedding of virulent organisms which in turn may infect other animals or their human handlers. Immunity to *Leptospira* is serovar specific, and although vaccines have been available for many years, most induce only a poor and short-lived immunity.

There is therefore a need for development of combination vaccines that provide protection against a large variety of antigens that are safe for pregnant and nursing cows and their offspring and meet dairy and beef cow market needs. The present invention provides vaccines for the treatment and prevention of the major infectious causes of respiratory and reproductive disease in animals, such as cows and calves. The present invention further provides immunogenic compositions and methods of treating or preventing diseases or disorders in animals.

SUMMARY OF THE INVENTION

The present invention provides a method of treating or preventing a disease or disorder in an animal caused by infection with at least one of, BVDV Type 1 or Type 2, BHV-1, PI3, BRSV, *Campylobacter fetus*, *Leptospira canicola*, *Leptospira grippotyphosa*, *Leptospira borgpetersenii hardjo-prajitno*, *Leptospira icterohaemmorrhagiae*, *Leptospira borgpetersenii hardjo-bovis* and *Leptospira interrogans pomona* comprising administering to the animal, an effective amount of a combination vaccine.

The present method provides protection to animals such as bovine, in particular, dairy cattle, against respiratory infection and reproductive disease. The present method provides protection to animals such as pregnant cows against abortion caused by IBR and persistent fetal infections caused by BVDV, Types 1 and 2. The present method also provides protection to animals such as lactating cows and calves nursing pregnant cows against persistent infections caused by BVDV, Types 1 and 2. Thus, the present method provides protection to breeding age animals, pregnant animals and lactating animals.

The combination vaccine employed in the present methods can be a whole or partial cell preparation (e.g., modified live preparation). The combination vaccine administered in accordance with the present invention may include additional components, such as an adjuvant and optionally a second or more antigens. A second antigen is selected from the following, including, but not limited, to bovine herpesvirus type 1 (BHV-1), bovine viral diarrhea virus (BVDV type 1 or 2), bovine respiratory syncitial virus (BRSV), parainfluenza virus (PI3), *Leptospira canicola*, *Leptospira grippotyphosa*, *Leptospira borgpetersenii hardio-prajitno*, *Leptospira icterohaemmorrhagia*, *Leptospira interrogans pomona*, *Leptospira borgpetersenii hardjo-bovis*, *Leptospira bratislava*, *Campylobacter fetus*, *Neospora cani-* num, *Trichomonus fetus*, *Mycoplasma bovis*, *Haemophilus somnus*, *Mannheimia haemolytica* and *Pasturella multocida*.

DETAILED DESCRIPTION OF THE INVENTION

The present invention provides a method of treating or preventing a disease or disorder in an animal caused by infection with IBR, BVDV, PI3, BRSV, *Campylobacter fetus* and/or Leptospirae by administering to the animal, an effective amount of a combination vaccine.

In certain embodiments, the vaccines used in the method of the present invention comprise a modified live vaccine and a pharmaceutically acceptable carrier, or a modified live vaccine and an adjuvant.

For clarity of disclosure, and not by way of limitation, the detailed description of the invention is divided into the following subsections which describe or illustrate certain features, embodiments or applications of the invention.

DEFINITIONS AND ABBREVIATIONS

The term "treating or preventing" with respect to a disease or disorder as used herein means reducing or eliminating the risk of infection by a virulent BVDV virus, types 1 and 2; IBR; PI3; BRSV; Campylobacteria; and/or *Leptospira* antigens, ameliorating or alleviating the symptoms of an infection, or accelerating the recovery from an infection. The treatment is considered therapeutic if there is a reduction in viral or bacterial load, decrease in pulmonary infections, reduced rectal temperatures, and/or increase in food uptake and/or growth. The treatment is also considered therapeutic if there is a reduction in fetal infection and urinary shedding due to infection with *Leptospira* serovars *hardjo* and *pomona*, for example.

The method of the present invention is, for example, effective in preventing or reducing abortion caused by IBR and infections caused by BVDV Types 1 and 2, and reducing rectal temperatures. The present invention is therefore contemplated to provide fetal protection against IBR and infections caused by BVDV Types 1 and 2 as well as fetal protection against cattle herpes and cattle pestiviruses. The present invention is also contemplated to provide protection against persistent fetal infection, such as persistent BVDV infection. By "persistent fetal infection" is meant infection occurring during early fetal development (e.g., 45-125 days of gestation) that leads to the live birth of animals that are immunotolerant to BVDV and maintain active BVDV replication and multiplication that often occurs at a high rate for months or years, serving as a permanent source of BVDV in the herd. These persistently infected animals are also at risk of developing fatal mucosal disease if superinfected with a cytopathic virus biotype.

The term "combination vaccine" is meant a bivalent or multivalent combination of antigens including modified live antigens and/or inactivated antigens. In accordance with the present invention a combination vaccine can comprise modified live infectious IBR, PI3, BRSV and inactivated BVDV Types 1 and 2, one or more antigens such as but not limited to *Leptospira canicola*, *Leptospira grippotyphosa*, *Leptospira borgpetersenii hardio-prajitno*, *Leptospira icterohaemmorrhagia*, *Leptospira interrogans pomona*, *Leptospira borgpetersenii hardjo-bovis*, *Leptospira bratislava*, *Campylobacter fetus*, *Neospora caninum*, *Trichomonus fetus*, *Mycoplasma bovis*, *Haemophilus somnus*, *Mannheimia haemolytica* and *Pasturella multocida*, a veterinary acceptable carrier and an adjuvant. In a preferred embodiment the modified live IBR component is temperature sensitive IBR. In another preferred embodiment the BVDV Type 2 component is cytopathic (cpBVD-2 strain 53637-ATCC No. PTA-4859) and the BVDV Type 1 component is cytopathic 5960 (cpBDV-1 strain 5960-National Animal Disease Center, United States Department of Agriculture, Ames, Iowa). The present invention also contemplates non-cytopathic BVDV Type 1 and Type 2 strains. In still another preferred embodiment, the modified live antigens are desiccated, lyophilized or vitrified.

In accordance with the present invention a combination vaccine can comprise inactivated BVDV Types 1 and 2, one or more antigens such as, but not limited to, *Leptospira canicola*, *Leptospira grippotyphosa*, *Leptospira borgpetersenii hardio-prajitno*, *Leptospira icterohaemmorrhagia*, *Leptospira interrogans pomona*, *Leptospira borgpetersenii hardjo-bovis*, *Leptospira bratislava*, *Campylobacter fetus*, *Neospora caninum*, *Trichomonus fetus*, *Mycoplasma bovis*, *Haemophilus somnus*, *Mannheimia haemolytica* and *Pasturella multocida*, a veterinary acceptable carrier and an adjuvant. The term "combination vaccine" as used herein also refers to a multicomponent composition containing at least one modified live antigen, at least one second antigen and an adjuvant which prevents or reduces the risk of infection and/or which ameliorates the symptoms of infection. In a preferred embodiment the second antigen is inactivated. In a preferred embodiment the source of the combination vaccine is PregSure® 5 (Pfizer, Inc.), PregSure®5-L5 (Pfizer, Inc.) and PregSure® 5-VL5 (Pfizer, Inc.). A particularly preferred source of the combination vaccine is PregSure® 5-VL5.

The protective effects of a combination vaccine composition against a pathogen are normally achieved by inducing in the subject an immune response, either a cell-mediated or a humoral immune response or a combination of both. Generally speaking, abolished or reduced incidences of BVDV, IBR, and/or PI3 infection, amelioration of the symptoms, or accelerated elimination of the viruses from the infected subjects are indicative of the protective effects of a combination vaccine composition. The vaccine compositions of the present invention provide protection against infections caused by either or both type 1 and type 2 BVD viruses as well as abortions caused by BHV-1 (IBR) and respiratory infections caused by PI3 and BRSV.

The present method of treating or preventing a disease or disorder in an animal caused by infection with IBR, BVDV, PI3, BRSV, *Campylobacter fetus* and/or Leptospirae by administering a combination vaccine is also referred to herein as a vaccination method.

The term "combination vaccine" that may be used in the present method can include, for example, an inactivated whole or partial *C. fetus* and/or *Leptospira* cell preparation, inactivated BVDV types 1 and 2 and/or one or more modified live antigens such as BHV-1, PI3 and/or BRSV.

In one embodiment, the vaccine compositions of the present invention include an effective amount of one or more of the above-described BVDV viruses, preferably cpBVD-2 strain 53637 (ATCC No. PTA-4859); cpBVD-1 strain 5960 (cpBDV-1 strain 5960-National Animal Disease Center, United States Department of Agriculture, Ames, Iowa); IBR ts mutant strain RBL 106 (National Institute of Veterinary Research, Brussels, Belgium); PI$_3$ ts mutant strain RBL 103 (RIT, Rixensart, Belgium); BRSV strain 375 (Veterinary Medical Research Institute, Ames, Iowa) Purified BVDV viruses can be used directly in a vaccine composition, or preferably, BVD viruses can be further attenuated by way of chemical inactivation or serial passages in vitro. Typically, a vaccine contains between about $1 \times 10^3$ and about $1 \times 10^{10}$ plaque or colony forming units of virus, with a veterinary acceptable carrier and an adjuvant, in a volume of between 0.5 and 5 ml and preferably about 2 ml. The precise amount of a virus in a vaccine composition effective to provide a protective effect can be determined by a skilled veterinary physician. Veterinary acceptable carriers suitable for use in vaccine compositions can be any of those described hereinbelow.

The typical route of administration will be intramuscular or subcutaneous injection of between about 0.1 and about 5 ml of vaccine. The vaccine compositions of the present invention can also include additional active ingredients such as other vaccine compositions against BVDV, e.g., those described in WO 9512682, WO 9955366, U.S. Pat. Nos. 6,060,457, 6,015,795, 6,001,613, and 5,593,873.

Vaccination can be accomplished by a single inoculation or through multiple inoculations. If desired, sera can be collected from the inoculated animals and tested for the presence of antibodies to BVD virus.

In another embodiment of the present invention, the vaccine compositions are used in treating BVDV infections. Accordingly, the present invention provides methods of treating infections in animal subjects caused by BVD viruses of type 1 or type 2, or a combination of type 1 and type 2, by administering to an animal, a therapeutically effective amount of a BVD virus of the present invention. In another embodiment the vaccine compositions of the present invention are effective for the improvement of herd fertility, and for the reduction of the risk of disease transmission from cattle to human handlers.

By "animal subject" is meant to include any animal that is susceptible to BVDV, BHV, $PI_3$, BRSV or *Leptospira* infections, for example, such as bovine, sheep and swine.

In practicing the present methods, a vaccine composition of the present invention is administered to a cattle preferably via intramuscular or subcutaneous routes, although other routes of administration can be used as well, such as e.g., by oral, intranasal (e.g. aerosol or other needleless administration), intra-lymph node, intradermal, intraperitoneal, rectal or vaginal administration, or by a combination of routes. Boosting regimens may be required and the dosage regimen can be adjusted to provide optimal immunization.

By "immunogenic" is meant the capacity of a BVD virus to provoke an immune response in an animal against type 1 or type 2 BVD viruses, or against both type 1 and type 2 BVD viruses. The immune response can be a cellular immune response mediated primarily by cytotoxic T-cells, or a humoral immune response mediated primarily by helper T-cells, which in turn activates B-cells leading to antibody production.

According to the present invention, the viruses are preferably attenuated by chemical inactivation or by serial passages in cell culture prior to use in an immunogenic composition. The methods of attenuation are well known to those skilled in the art.

A preferred virus to be included in an immunogenic composition of the present invention is BVDV cp53637 (ATCC No. PTA-4859). Another preferred virus to be included in an immunogenic composition of the present invention is BVDV 5960. A further preferred virus to be included in an immunogenic composition of the present invention is IBR strain is mutant strain RBL 106. Another preferred virus to be included in an immunogenic composition of the present inventions is $PI_3$ is mutant strain RBL 103. Yet another preferred virus to be included in an immunogenic composition of the present invention is BRSV strain 375.

The immunogenic compositions of the present invention can also include additional active ingredients such as other immunogenic compositions against BVDV, e.g., those described in copending application Ser. No. 08/107,908, WO 9512682, WO 9955366, U.S. Pat. Nos. 6,060,457, 6,015,795, 6,001,613, and 5,593,873.

In addition, the immunogenic and vaccine compositions of the present invention can include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others. Adjuvants include, but are not limited to, the RIBI adjuvant system (Ribi Inc.), alum, aluminum hydroxide gel, Cholesterol, oil-in water emulsions, water-in-oil emulsions such as, e.g., Freund's complete and incomplete adjuvants, Block co-polymer (CytRx, Atlanta Ga.), SAF-M (Chiron, Emeryville Calif.), AMPHI-GEN® adjuvant, saponin, Quil A, QS-21 (Cambridge Biotech Inc., Cambridge Mass.), GPI-0100 (Galenica Pharmaceuticals, Inc., Birmingham, Ala.) or other saponin fractions, monophosphoryl lipid A, Avridine lipid-amine adjuvant, heat-labile enterotoxin from *E. coli* (recombinant or otherwise), cholera toxin, or muramyl dipeptide, among many others. The immunogenic compositions can further include one or more other immunomodulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, the present invention contemplates compositions comprising from about 50 µg to about 2000 µg of adjuvant and preferably about 500 µg/2 ml dose of the vaccine composition. In another preferred embodiment, the present invention contemplates vaccine compositions comprising from about 1 µg/ml to about 60 µg/ml of antibiotic, and more preferably less than about 30 µg/ml of antibiotic.

The immunogenic compositions of the present invention can be made in various forms depending upon the route of administration. For example, the immunogenic compositions can be made in the form of sterile aqueous solutions or dispersions suitable for injectable use, or made in lyophilized forms using freeze-drying techniques. Lyophilized immunogenic compositions are typically maintained at about 4° C., and can be reconstituted in a stabilizing solution, e.g., saline or and HEPES, with or without adjuvant.

The immunogenic compositions of the present invention can be administered to animal subjects to induce an immune response against type 1 or type 2 BVD viruses, or against both type 1 and type 2 BVD viruses. Accordingly, another embodiment of the present invention provides methods of stimulating an immune response against type 2 or type 2 BVD viruses, or against a combination of type 1 and type 2 BVD viruses by administering to an animal subject an effective amount of an immunogenic composition of the present invention described above. By "animal subject" is meant to include any animal that is susceptible to BVDV infections, such as bovine, sheep and swine.

In accordance with the methods of the present invention, a preferred immunogenic composition for administration to an animal subject includes the BVDV cp53637 virus and/or the BVDV cp5960 virus. An immunogenic composition containing a BVDV virus, preferably attenuated by chemical inactivation or serial passage in culture, is administered to a cattle preferably via intramuscular or subcutaneous routes, although other routes of administration can be used as well, such as e.g., by oral, intranasal, intra-lymph node, intradermal, intraperitoneal, rectal or vaginal administration, or by a combination of routes.

Immunization protocols can be optimized using procedures well known in the art. A single dose can be administered to animals, or, alternatively, two or more inoculations can take place with intervals of two to ten weeks. Depending on the age of the animal, the immunogenic or vaccine composition can be readministered. For example, the present invention contemplates the vaccination of healthy cattle prior to six months of age and revaccination at six months of age. In another example, the present invention contemplates the vaccination of prebreeding cattle at about 5 weeks prebreeding and again at about 2 weeks prebreeding to protect a fetus against infection caused by BVDV Types 1 and 2. Semiannual revaccination with a single dose of the combination vaccine is also contemplated to prevent BVDV fetal infection.

The extent and nature of the immune responses induced in the cattle can be assessed by using a variety of techniques. For example, sera can be collected from the inoculated animals and tested for the presence of antibodies specific for BVDV viruses, e.g., in a conventional virus neutralization assay.

The term "cattle" as used herein refers to bovine animals including but not limited to steer, bulls, cows, and calves. Cattle as used herein refers to pregnant and lactating bovine animals. Preferably, the method of the present invention is applied to an animal which is a non-human mammal; preferably, a lactating or pregnant cow and its fetus.

The term "therapeutically effective amount" or "effective amount" refers to an amount of combination vaccine sufficient to elicit an immune response in the animal to which it is administered. The immune response may comprise, without limitation, induction of cellular and/or humoral immunity. The amount of a vaccine that is therapeutically effective may vary depending on the particular virus used, the condition of the cattle and/or the degree of infection, and can be determined by a veterinary physician.

Inactivated (Partial or Whole cell) and Modified Live Vaccines.

Inactivated or modified live vaccines for use in the method of the present invention can be prepared using a variety of methods which are known in the art.

For example, BVDV isolates can be obtained directly from infected cow uteri using known techniques.

BVDV isolates can be inactivated using a variety of known methods, e.g., treating the bacterial isolate with binary ethyleneimine (BEI) as described in U.S. Pat. No. 5,565,205, or inactivation with formalin, glutaraldehyde, heat, irradiation, BPL, or other inactivating agents known to the art.

In addition to inactivated viral isolates, a vaccine product can also include an appropriate amount of one or more commonly used adjuvants. Suitable adjuvants may include, but are not limited to: mineral gels, e.g., aluminum hydroxide; surface active substances such as lysolecithin; glycosides, e.g., saponin derivatives such as Quil A or GPI-0100; pluronic polyols; polyanions; non-ionic block polymers, e.g., Pluronic F-127 (B.A.S.F., USA); peptides; mineral oils, e.g. Montanide ISA-50 (Seppic, Paris, France), carbopol, Amphigen, Amphigen Mark II (Hydronics, USA), Aihydrogel, oil emulsions, e.g. an emulsion of mineral oil such as BayolF/Arlacel A and water, or an emulsion of vegetable oil, water and an emulsifier such as lecithin; alum; bovine cytokines; cholesterol; and combinations of adjuvants. In a preferred embodiment, the saponin containing oil-in-water emulsion is conventionally microfluidized.

A particularly preferred source of BVDV type 1, for use in the vaccine and method of the present invention is PregSure® (PFIZER INC.), containing BVDV strain 5960 (acquired from the National Animal Disease Center (NADC), USDA, Ames, Iowa). A particularly preferred source of BVDV type 2, for use in the vaccine and method of the present invention is PregSure® (Pfizer, Inc.), containing BVDV strain 53637 (ATCC No. PTA-4859), acquired from the University of Guelph, Guelph, Ontario.

Preferably, the strains 5960 and 53637 are inactivated with BEI and adjuvanted with a commercially available adjuvant, preferably, Quil A-Cholesterol-Amphigen (Hydronics, USA). A preferred dose of the immunogenic and vaccine compositions of the present invention is about 2.0 ml. Preservatives can be included in the methods and compositions of the present invention. Preservatives contemplated by the present invention include gentamicin and merthiolate. A carrier can also be added, preferably, PBS. Preparation of modified live vaccines, such as by attenuation of virulent strains by passage in culture, is known in the art.

Inactivated BVDV isolates can also be combined with the following bacteria and viruses, including but not limited to, bovine herpesvirus type 1 (BHV-1), bovine respiratory syncitial virus (BRSV), parainfluenza virus (PI3), *Campylobacter fetus, Leptospira canicola, Leptospira grippotyphosa, Leptospira borgpetersenii hardjo-prajitno, Leptospira icterohaemmorrhagiae, Leptospira borgpetersenii hardjo-bovis* and *Leptospira interrogans pomona*.

Dosing and Modes of Administration

According to the present invention, an effective amount of a combination vaccine administered to cattle, including pregnant cows and calves nursing pregnant cows provides effective immunity against disease and fetal infection associated with Bovine Viral Diarrhea Virus (Type 1 and 2). In one embodiment, the combination vaccine is administered to calves in two doses at an interval of about 3 to 4 weeks. For example, the first administration is performed when the animal is about 1 to about 3 months of age. The second administration is performed about 1 to about 4 weeks after the first administration of the combination vaccine.

In a preferred embodiment, the first administration is performed about 5 weeks prior to animal breeding. The second administration is performed about 2 weeks prior to animal breeding. Administration of subsequent vaccine doses is preferably done on an annual basis. In another preferred embodiment, animals vaccinated before the age of about 6 months should be revaccinated after 6 months of age. Administration of subsequent vaccine doses is preferably done on an annual basis.

The amount of combination vaccine that is effective depends on the ingredients of the vaccine and the schedule of administration. Typically, when an inactivated Bovine Viral Diarrhea Virus preparation is used in a vaccine, an amount of the vaccine containing about $10^3$ to about $10^{10}$ colony forming units per dose of BVDV, and preferably about $10^5$ to about $10^8$ colony forming units per dose of BVD V (Type 1 and 2) is effective when administered twice to the animal during a period of about 3 to 4 weeks. Preferably, a combination vaccine that provides effective immunity contains about $10^5$ to $10^8$ colony forming units/dose of BVDV (Type 1 and 2) and more preferably, about $10^6$ colony forming units/dose, when administered twice to the animal during a period of about 3 to 4 weeks. The first administration is performed about 5 weeks prior to animal breeding. The second administration is performed about 2 weeks prior to animal breeding. Administration of subsequent vaccine doses is preferably done on an annual basis. Animals vaccinated before the age of about 6 months should be revaccinated after 6 months of age. Administration of subsequent vaccine doses is preferably done on an annual basis.

According to the present invention, when the preferred product, PregSure® 5 (Pfizer, Inc.), is administered, PregSure® 5 is administered preferably twice, each time in the amount of about 0.5 ml to about 5.0 ml, preferably about 1.5 ml to about 2.5 ml, and more preferably, about 2 ml. When the preferred product PregSure® 5-L5 or PregSure® 5-VL5 is administered, PregSure® 5-L5 or PregSure® 5-VL5 is administered preferably twice, each time in the amount of about 0.5 ml to about 10.0 ml, preferably about 3 ml to about 7 ml, and more preferably, about 5 ml. The first administration is performed about 5 weeks prior to animal breeding. The second administration is performed about 2 weeks prior to animal breeding. Administration of subsequent vaccine doses is preferably done on an annual basis. Animals vaccinated before the age of about 6 months should be revaccinated after 6 months of age. Administration of subsequent vaccine doses is preferably done on an annual basis.

In accordance with the present invention, administration can be achieved by known routes, including the oral, intranasal, topical, transdermal, and parenteral (e.g., intravenous, intraperitoneal, intradermal, subcutaneous or intramuscular). A preferred route of administration is subcutaneous or intramuscular administration.

The present invention also contemplates a single primary dose followed by annual revaccination, which eliminates the necessity of administration of additional doses to calves prior to annual revaccination in order to generate and/or maintain immunity against infection.

The combination vaccine administered in accordance with the present invention can include additional components, such as an adjuvant (e.g., mineral gels, e.g., aluminum hydroxide; surface active substances such as Cholesterol, lysolecithin; glycosides, e.g., saponin derivatives such as Quil A, QS-21 or GPI-0100; pluronic polyols; polyanions; non-ionic block polymers, e.g., Pluronic F-127; peptides; mineral oils, e.g. Montanide ISA-50, carbopol, Amphigen, Alhydrogel, oil emulsions, e.g. an emulsion of mineral oil such as BayolF/Arlacel A and water, or an emulsion of vegetable oil, water and an emulsifier such as lecithin; alum; bovine cytokines; and combinations of adjuvants.).

According to the present invention, the administration of an effective amount of a combination vaccine administered to cattle at approximately 3 months of age provides effective immunity against respiratory infections and reproductive disease, and reduces abortions. The present invention also provides a method of immunizing cattle, including but not limited to cows, calves, and prebreeding heifers, against infection caused by BVDV (types 1 and 2), and respiratory disease attributed to IBR, BVDV (Types 1 and 2), PI3, BRSV, campylobacteriosis and leptospiriosis comprising administering to the animal at least one dose, and preferably two doses of the combination vaccine in order to immunize the animal against infection caused by BVD (types 1 and 2), IBR, PI3, BRSV, *Leptospira canicola, Leptospira grippotyphosa, Leptospira borgpetersenii hardio-prajitno, Leptospira icterohaemmorrhagia, Leptospira interrogans pomona, Leptospira borgpetersenii hardjo-bovis, Leptospira bratislava*, and *Campylobacter fetus*.

In a preferred embodiment, the vaccine is administered subcutaneously. In another preferred embodiment, the vaccine is administered intramuscularly. Moreover, it is preferred that the vaccine dose comprise about 2 ml to about 7 ml, and preferably about 5 ml, each ml containing about $10^3$ to about $10^{10}$ colony forming units/per dose of virus. In another preferred embodiment the vaccine comprises about 2 ml, each ml containing about $10^3$ to about $10^{10}$ colony forming units per dose of virus. The combination vaccine is desirably administered twice to the animal; once at about 1 to about 3 months of age, and once at about 1 to 4 weeks later. The present invention also contemplates semiannual revaccinations with a single dose and revaccination prior to breeding.

The present invention also provides a method of protecting bovine fetuses against fetal infection and persistent fetal infection, comprising administering to the animal at least one dose, and preferably two doses of the combination vaccine in order to immunize the fetus against infection caused by BVD (types 1 and 2), IBR, PI3, BRSV, *Leptospira canicola, Leptospira grippotyphosa, Leptospira borgpetersenii hardio-prajitno, Leptospira icterohaemmorrhagia, Leptospira interrogans pomona, Leptospira borgpetersenii hardjo-bovis, Leptospira bratislava*, and *Campylobacter fetus*. The combination vaccine is desirably administered twice to the animal, once about five weeks prior to breeding and once at about two weeks prior to breeding.

The present invention also contemplates that the administration of an effective amount of a combination vaccine administered to animals, and preferably cattle to treat or prevent disorders including persistent fetal infections and reproductive disorders, such as abortions in such animals.

The present invention is further illustrated, but not limited by the following examples.

EXAMPLE 1

Materials and Methods

Animals—Fifty-six BVDV seronegative (i.e., having serum neutralization [SN] titers<1:2) cows suitable for breeding were obtained from multiple sources and maintained in research isolation facilities for the duration of the study. Each animal was identified with duplicate ear tags, one placed in each ear. New tags were installed in cases where an animal lost an ear tag. Prior to the study, test animals were inoculated with commercial vaccines for leptospirosis, campylobacteriosis (vibriosis), and clostridial infections. Test animals were maintained under supervision of an attending veterinarian, who clinically monitored them on a daily basis.

Test vaccine—The test vaccine was a multivalent, modified live infectious bovine rhinotracheitis (IBR)-parainfluenza 3 (PI3)-respiratory syncytial virus (RSV) vaccine in desiccated form, rehydrated with an inactivated, liquid BVDV vaccine combined with an adjuvant. (Pfizer Inc, New York, N.Y.) The BVDV component contained the minimum BVDV-1 and -2 immunizing doses, combined with a sterile adjuvant. Potency of the BVDV immunizing antigens was established by calculating the geometric mean titer (GMT) for 8 replicate titrations of the bulk fluid used for vaccine preparation. Following rehydration, the IBR-PI3-BRSV-BVDV vaccine was administered in 2 mL doses by either intramuscular (IM) or subcutaneous (SC) injection. The desiccated IBR-PI3-RSV vaccine reconstituted with sterile water was used as a placebo, and was given by IM injection.

Challenge virus—A noncytopathic BVDV type 2 field isolate (Strain 94B-5359, obtained from Dr. Hana Van Campen, Wyoming State Veterinary Laboratory, University of Wyoming) was used as a challenge agent. Virus identity was confirmed by SN assay and reverse transcriptase polymerase chain reaction (RT-PCR). The RT-PCR analysis was positive for BVDV type 2 nucleotide sequences for the p125 protein and the 5 untranslated region, and negative for the BVDV type 1 gp53 and p80 conserved sequences. Challenge virus potency was established at a GMT of $10^{3.2}$ $TCID_{50}$/mL by 2 replicate titrations made immediately before and after challenge. Challenge inoculum was given intranasally in a 4 mL divided dose, 2 mL per nostril.

Serologic assays—Serum neutralization titers for BVDV types 1 and 2 were determined by a constant-virus, decreasing-serum assay in bovine cell culture. Serial dilutions of serum were combined with either 50-300 $TCID_{50}$ of cytopathic BVDV type 1 strain 5960, or a similar amount of cytopathic BVDV type 2 strain 125c.

Virus isolation—Postchallenge (PC) isolation of BVDV in bovine cell culture was attempted from peripheral cow blood, amniotic fluid, fetal blood, and fetal tissues. A BVDV-positive cell culture was determined by indirect immunofluorescence using goat anti-BVDV polyclonal antibodies. Isolation of BVDV from fetal tissues was also attempted using immunohistochemistry methods previously described. (Haines D M, Clark E G, and Dubovi E J. Vet Pathol 1992; 29:27-32.) Whole blood from cows was drawn from the jugular vein in 5-10 mL samples and placed in heparin-containing tubes for preparation of buffy coat cells used for virus isolation attempts. Amniotic fluid was collected under local anesthesia by left-flank laparotomy and aspiration of a 3-5 mL sample from the uterus.

Following caesarian section or spontaneous abortion, the eyes, spleen, thymus, and 3 brain sections (brainstem/midbrain, cerebrum, and cerebellum) were aseptically collected from each fetus. Supernatant from homogenized fetal tissues was used for virus isolation attempts in cell culture. For purposes of immunohistochemistry evaluation, fetal tissues were embedded in paraffin and tested in duplicate using 1:800 and 1:600 ascites dilutions containing anti-BVDV monoclonal antibodies.

Biometric data analysis—To demonstrate protection following challenge, a statistically significant reduction in incidence of maternal and fetal BVDV type 2 infection had to be demonstrated in vaccinated groups (T2 and T3) versus the placebo control group (T1). A Fisher's exact test was used to compare incidence of (1) cow viremia during the first 14 days following challenge, (2) BVDV isolation from amniotic fluid, (3) BVDV isolation from fetal tissue and fetal blood following spontaneous abortion or caesarian section, and (4) BVDV-positive fetal tissue immunohistochemistry. Serum neutralization titers were analyzed using a mixed linear model with repeated measures. Least squares means from the analysis of variance were used to calculate a geometric mean titer (GMT), which excluded SN data for cows that were not challenged. A probability value of $P \le 0.05$ was used to determine statistical significance.

Fetal protection study—The 56 test cows were randomly assigned to one of three test groups, an IM placebo group (T1), an IM vaccination group (T2), and a SC vaccination group (T3) as noted in Table 1. Cows were inoculated with either vaccine or placebo on study Day 0 and Day 21. In all cases, the Day 0 inoculation was administered on the left side of the neck, and the Day 21 inoculation was administered on the right side of the neck.

On Day 1, cows were given feed top-dressed with melengestrol acetate for 14 days. On Day 32, all cows received an IM prostaglandin injection (Lutalyse, Pharmacia & Upjohn, Kalamazoo, Mich.) to synchronize estrus. Cows which displayed estrus were bred by artificial insemination with certified BVDV-negative semen. On Day 100, at approximately 65 days of gestation, the pregnancy status of cows was determined by rectal palpation. On Day 105, 23 cows with confirmed pregnancies were randomly selected from each test group (7 controls, 8 IM vaccinates, and 8 SC vaccinates), relocated to a nearby isolation facility, (Midwest Veterinary Services, Oakland, Nebr.) and comingled. On Day 119, the 23 test cows were challenged by intranasal inoculation of virulent BVDV. Blood samples were collected on the day of challenge and at 8 PC intervals, on Days 119, 121, 123, 125, 127, 129, 133, 140, and 147 (PC days 0, 2, 4, 6, 8, 10, 14, 21, and 28) for purposes of BVDV isolation and serologic assay.

On Day 147 (28 days after challenge), left flank laparotomies were performed and amniotic fluid was extracted from each cow. On Day 297, approximately 7-14 days prior to anticipated calving, test cows were transported to facilities at the University of Nebraska, Department of Veterinary and Biomedical Services, for caesarian section. Immediately prior to surgery, a blood sample was collected from each cow for SN assay. Following caesarian delivery (on Days 300-301), a blood sample was collected from each fetus. Fetuses were then euthanized and tissues were aspecticaly collected for purposes of BVDV isolation.

In some cases where spontaneous abortions occurred, blood samples were taken from the dam when abortion was detected and two weeks later. The paired blood samples were submitted for serologic testing (University of Nebraska Veterinary Diagnositic Center, Lincoln, Nebr.) and aborted fetuses were evaluated for BVDV isolation (Pfizer Central Research, Lincoln, Nebr.) and histopathologic evaluation of fetal tissues (Saskatoon Veterinary Biodiagnostics, Saskatoon, SK, Canada).

Results

No adverse events were observed during or immediately following administration of the 2 vaccine doses.

All cows were seronegative to BVDV types 1 and 2 prior to vaccination (Day 0), confirming that the test animals were immunologically naïve to BVDV at the outset of the study. The GMT values for BVDV type 1 are shown in Table 2. Fifteen of 16 vaccinates seroconverted following 2 vaccine doses. Cow number 61 (T3 group) had BVDV type 1 SN titers of <1:2 on Day 0, 1:19 on Day 21, and <1:2 on Day 33 and Day 119. The GMT values to BVDV type 2 are shown in Table 3. All vaccinates, including cow 61, seroconverted following the second dose. (Cow 61 had BVDV type 2 SN titers of <2 on Day 0, 1:19 on Day 21, 1:2,048 on Days 33, and 1:431 on Day 119.) At breeding (Days 32-41), vaccinated cows (excluding cow 61) had BVDV type 1 SN titers ranging from 1:64 to 1:13,777. Vaccinated cows had BVDV type 2 titers ranging from 1:64 to 1:6,889 at a breeding. Following vaccination, the difference in GMT values for the IM (T2) versus SC (T3) groups was not statistically significant at either of 2 prechallenge intervals or following challenge. All cows in the placebo group (T1) remained seronegative for both BVDV types 1 and 2 up to the time of challenge (Day 119), indicating that the study was not compromised by adventitious exposure. All placebo cows responded serologically to challenge, verifying that a viable challenge occurred in each animal. The placebo group had a PC-GMT for BVDV type 1 that was significantly lower than the anemnestic responses achieved by either vaccine group (Table 2, Day 147). Placebo cows also had a lower PC-GMT to BVDV type 2 compared to either vaccine group, but the difference was statistically significant only versus the IM (T2) vaccinates.

Twenty-three cows in the 3 test groups were confirmed pregnant, challenged, and subjected to amniocentesis (Table 1). Between the time of amniocentesis (Day 147) and caesarian section (Day 300-301), 7 cows aborted, 4 from the T2 group and 3 from the T3 group. In addition, 3 bred cows (1 T1 placebo cow and 2 cows from the T3 group) were found to be not pregnant at the time of caesarian section. These 3 cows were confirmed pregnant by rectal palpation on Day 100, approximately 65 days after breeding, indicating that subsequent undetected abortion or fetal resorption occurred. Because fetal tissues from the 3 cows with failed pregnancies were not available for evaluation, these animals were removed from the study. On Day 259, T1 placebo cow number 67 died, and its fetus was removed for purposes of BVDV isolation. Thus, at the conclusion of the study, 12 of the 23 cows that had been challenged underwent caesarian section. The 12 caesarian derived fetuses plus the 7 aborted fetuses and the fetus from the dead cow (20 in all) were evaluated for BVDV isolation.

Cow 38 from the T2 group aborted its fetus on Day 156 (at 123 days of gestation, and 37 days after challenge). Paired serum samples were not evaluated, but cow 38 was negative for postchallenge BVDV isolation from peripheral blood and amniotic fluid. The fetus was severely autolyzed. Histopathologic and bacteriologic evaluation of the fetus revealed purulent inflammation of the chorionic and subchorionic connective tissues. *Staphylococcus hyicus* was isolated from the lung, liver, and thoracic fluid. Negative BVDV isolation and immunohistochemistry results were obtained, indicating that the fetus was not infected as a result of challenge.

Three T3 cows (numbers 21, 27, and 40) aborted on Days 158 or 159 (at 125-127 days of gestation, and 39 or 40 days after challenge). The abortions were not observed, so the recovered fetuses could not be attributed to specific cows. They were designated unknown fetuses 1, 2 or 3. Unknown fetus 1 was mummified, with lesions histologically typical of neosporosis. Unknown fetus 2 was autolyzed, with multifocal purulent and necrotizing placentitis and large numbers of bacterial cocci mixed with inflammatory exudate. *Staphylococcus hyicus* was isolated from lung, kidney, liver, stomach contents and placental tissue. Unknown fetus 3 was macerated and autolyzed. *Staphylococcus* sp was isolated from the lung, liver, kidney, and stomach contents. Negative BVDV isolation and immunohistochemistry results were obtained for all tissues from the 3 unknown fetuses. All 3 dams were negative for postchallenge BVDV isolation from peripheral blood. Cows 21 and 40 were likewise negative for BVDV isolation from amniotic fluid, but cow 27 had a BVDV-positive amniotic fluid sample. Paired serum samples from the dams were not evaluated.

Cow 45 from the T2 group aborted its fetus on Day 160 (at 128 days of gestation, and 41 days after challenge). Extensive fetal autolysis was evident. *Staphylococcus* sp was isolated from the lung, liver, kidney, stomach contents, and placenta. Placentitis with multifocal thrombosis and suppurative vascultisis was present. Serologic assays of thoracic fluid were negative for IBR, bovine viral diarrhea (BVD), and leptospirosis. Negative BVDV isolation and immunohistochemistry results were obtained for all fetal tissues.

Cow 66 from the T2 group aborted its fetus on Day 195 (at 160 days of gestation, and 76 days after challenge). Marked suppurative inflammation of the placental lamina propria extending from the fetal surface was observed. *E. coli* and *Proteus vulgaris* were cultured from the stomach contents and placenta. Paired serum samples and thoracic fluid serology results did not support IBR, BVD, or leptospirosis as an etiology. Negative BVDV isolation and immunohistochemistry results were obtained for all fetal tissues.

Cow 31 from the T2 group aborted its fetus on Day 295 (at 262 days of gestation, and 176 days after challenge). Histopathologic examination revealed diffuse necropurulent placentitis, necrosis of the chorionic epithelium, and intense neutrophilic inflammation. Gram-negative coccobacilli and rods were cultured from the inflammatory foci. Paired serology results did not support IBR, BVD, or leptospirosis as an etiology. Negative BVDV isolation and immunohistochemistry results were obtained for all fetal tissues.

Positive BVDV isolation was obtained from PC peripheral blood samples and amniotic fluid obtained from T1 placebo cow 67, which died prior to the conclusion of the study. All fetal tissues from this cow were BVDV isolation and immunohistochemistry positive.

Blood samples collected from the 12 caesarian derived fetuses were assayed for SN titers to BVDV type 1 and 2. None of the caesarian derived fetuses from the 5 placebo cows or 7 vaccinates was seropositive for either BVDV type 1 or 2.

Postchallenge virus isolation results are shown in Table 4. All 7 T1 placebo cows experienced BVDV viremia, corroborating serologic results indicating that a viable challenge occurred in each of the nonvaccinated animals. Blood samples from all 16 of the T2 and T3 vaccinates were negative for BVDV viremia on each of 8 postchallenge samples. The difference in the rate of PC viremia in T2 and T3 vaccinates versus controls was statistically significantly ($P \leq 0.0001$).

Amniotic fluid from 2 of 16 (12.5 percent) vaccinates was BVDV positive, versus positive results for 7 of 7 (100 percent) T1 placebo cows, a statistically significant difference ($P \leq 0.0001$). Amniotic fluid samples from T3 vaccinates 27 and 60 were positive. The fetus from cow 27 was BVDV-negative by virus isolation and immunohistochemistry methods.

Fetal tissues from 1 of 14 vaccinates (7.1 percent), T3 cow 60, were positive for BVDV isolation. This compared to BVDV isolation in 6 of 6 (100 percent) fetuses from T1 placebo cows, a statistically significant difference ($P \leq 0.0001$). BVDV isolation results were either all positive or all negative for the fetal tissues evaluated from each fetus.

Immunohistochemistry results were BVDV positive for fetal tissues from 1 of 14 (7.1 percent) T2 and T3 vaccinates (T3 cow 60). All fetal tissues from 6 of 6 (100 percent) T1 placebo cows were BVDV-immunohistochemistry positive, a significantly higher incidence ($P \leq 0.0001$) versus the vaccinates. BVDV immunohistochemistry results were either all positive or all negative for the tissues evaluated from each fetus.

Table 5 indicates the source of virus isolation and the prechallenge SN titers of the 2 vaccinated cows with positive BVDV isolation results. Serologic data indicates that T3 vaccinates 27 and 60 both responded immunologically to vaccination. Cow 27 had a BVDV type 2 SN titer at challenge that was lower than the GMT for the T3 group, but the difference was not significant.

Intramuscular and SC vaccination collectively provided 92.9 percent efficacy against fetal BVDV-2 infection, with negative BVDV isolation results occurring in fetal tissues from 13 of 14 vaccinated cows (Table 4). This compared to a 88.9 percent rate of protection (16 of 18 vaccinates were BVDV-isolation negative) in an earlier test of the same vaccine against fetal challenge with BVDV-1 (see Example 2). In both of these studies, 100 percent fetal infection occurred in nonvaccinated placebo cows, affirming that vaccinates were exposed to a severe challenge of immunity.

Challenge virus was isolated from the amniotic fluid of 2 vaccinates, cows 27 and 60 (Table 5). As a result, both of these cows were considered positive for BVDV infection, even though they were viremia negative at each of 8 PC intervals. Virus isolation, as well as immunohistochemistry methods of high specificity and sensitivity, did not detect BVDV in the aborted fetus from cow 27, so it was of necessity reported as BVDV-negative. Abortion of this fetus due to a BVDV infectious process in the dam was possible.

To corroborate results, two methods were used to assess protection in cows (viremia and virus isolation from amniotic fluid) and their fetuses (immunohistochemistry and virus isolation in tissue culture). The most conservative result was used to determine rate of protection. Thus, the protection rate in vaccinated cows was considered to be 87.5 percent (14 of 16), the percentage of cows negative for virus isolation from amniotic fluid, rather than 100 percent, the percentage of viremia-negative cows. No published BVDV challenge-of-immunity study has yielded 100 percent fetal protection in vaccinates against challenge that produced 100 percent fetal infection in nonvaccinated controls. Even a modified-live virus (MLV) vaccine, not commonly evaluated in pregnant cows, provided no more than 83 percent protection against fetal BVDV-1 infection in one study. (Cortese V S, Grooms, D L, Ellis J, et al (1998) Am J Vet Res. 59:1409-1413.)

TABLE 1

Test groups and final pregnancy status of cows in bovine viral diarrhea virus (BVDV) type 2 fetal challenge study

| Group | Treatment | No. cows vaccinated (Days 0, 21) | No. cows challenged (Day 119) | (1) Maternal death$^a$ | (2) Abortion$^b$ | (3) Failed pregnancy$^c$ | (4) Caesarian section | No. fetuses evaluated for BVDV isolation (1 + 2 + 4) |
|---|---|---|---|---|---|---|---|---|
| T1 | Placebo (IM) | 18 | 7 | 1 | 0 | 1 | 5 | 6 |
| T2 | Vaccine (IM) | 18 | 8 | 0 | 4 | 0 | 4 | 8 |
| T3 | Vaccine (SC) | 20 | 8 | 0 | 3 | 2 | 3 | 6 |

IM = intramuscular vaccination;

SC = subcutaneous vaccination $^a$Maternal death occurred for T1 cow 67 (Day 259).

$^b$Abortions occurred in T2 cows 38 (Day 156), 45 (Day 160), 66 (Day 195), 31 (Day 295) and in T3 cows 21, 27, and 40 (Days 158 or 159).

$^c$All cows with failed pregnancies were confirmed pregnant on Day 100, approximately 65 days after breeding.

TABLE 2

Bovine viral diarrhea virus (BVDV) type 1 serological response in cows challenged with BVDV type 2

| | | Reciprocal of BVDV type 1 serum neutralizing (SN) geometric mean titer at selected test intervals | | | | | |
|---|---|---|---|---|---|---|---|
| Treatment group | No. seropositive cows on day of breeding$^a$ | Vaccination (Day 0) | Vaccination (Day 21) | Breeding (Days 32-41) | Challenge (Day 119) | Amniocentesis (Day 147) | Caesarian section (Days 300-301) |
| T1 (n = 7) | 0/7 | <2 | <2 | <2 | <2 | 65.7 | 833.6 (n = 6)$^d$ |
| T2 (n = 8) | 8/8 | <2 | 13.7$^b$ | 2,383.1$^c$ | 480.7$^c$ | 1,919.2$^c$ | 762.7 (n = 4)$^e$ |
| T3 (n = 8) | 7/8 (87.5%) | <2 | 18.2$^c$ | 1,116.6$^c$ | 570.4$^c$ | 1,448.3$^c$ | 691.7 (n = 5)$^f$ |
| T2 & T3 (n = 16) | 15/16 (93.8%) | <2 | 15.8$^c$ | 1,631.3$^c$ | 523.6$^c$ | 1,667.2$^c$ | 726.3 (n = 9) |

$^a$SN titer reciprocal ≥8.

$^b$Statistically significant difference vs. placebo group (T1), P ≤ 0.0002.

$^c$Statistically significant difference vs. placebo group (T1), P ≤ 0.0001.

$^d$Cow 67 died on Day 259.

$^e$Abortions occurred for cows 38 (Day 156), 45 (Day 160), 66 (Day 195), and 31 (Day 295); blood was not collected from these cows on Day 300-301.

$^f$Abortions occurred for cows 21, 27, and 40 on Days 158 and Day 159; blood was not collected from these cows on Day 300-301.

TABLE 3

Bovine viral diarrhea virus (BVDV) type 2 serological response in cows challenged with BVDV type 2

Reciprocal of BVDV type 2 serum neutralizing (SN) geometric mean titer at selected test intervals

| Treatment group (no.) | No. seropositive cows on day of breeding[a] | Vaccination (Day 0) | Vaccination (Day 21) | Breeding (Days 32-41) | Challenge (Day 119) | Aminocentesis (Day 147) | Caesarian section (D |
|---|---|---|---|---|---|---|---|
| T1 (n = 7) | 0/7 | <2 | <2 | <2 | <2 | 402.6 | 2,823.8 (n = 6)[g] |
| T2 (n = 8) | 8/8 | <2 | 7.0[b] | 1,217.7[d] | 285.2[d] | 2,598.6[e] | 922.2b (n = 4)[h] |
| T3 (n = 8) | 8/8 | <2 | 12.8[c] | 1,837.6[d] | 261.7[d] | 1,217.5 | 621.3 (n = 5)[i] |
| T2 & T3 (n = 16) | 16/16 | <2 | 9.5[c] | 1,495.9[d] | 273.2[d] | 1,778.7[f] | 756.9[b] (n = 9) |

[a]SN titer reciprocal ≥8.
[b]Statistically significant difference vs. placebo group (T1), P ≤ 0.0064.
[c]Statistically significant difference vs. placebo group (T1), P ≤ 0.0005.
[d]Statistically significant difference vs. placebo group (T1), P ≤ 0.0001.
[e]Statistically significant difference vs. placebo group (T1), P = 0.0128.
[f]Statistically significant difference vs. placebo group (T1), P = 0.023.
[g]Cow 67 died on Day 259.
[h]Abortions occurred for cows 38 (Day 156), 45 (Day 160), 66 (Day 195), and 31 (Day 295); blood was not collected from these cows on Day 300-301.
[i]Abortions occurred for cows 21, 27, and 40 on Days 158 and Day 159; blood was not collected from these cows on Day 300-301.

TABLE 4

Summary of postchallenge cow and fetal bovine viral diarrhea virus (BVDV) isolation results Postchallenge virus isolation method and incidence

| Treatment group | Viremia in cows[a] | Amniotic fluid virus isolation | Fetal tissue virus isolation[b] | Fetal tissue immunohisto-chemistry[b] |
|---|---|---|---|---|
| T1 Placebo (IM) | 7/7 (100%) | 7/7 (100%) | 6/6 (100%)[c] | 6/6 (100%)[c] |
| T2 Vaccine (IM) | 0/8 (0%)[d] | 0/8 (0%)[d] | 0/8 (0%)[d] | 0/8 (0%)[d] |
| T3 Vaccine (SC) | 0/8 (0%)[d] | 2/8 (25%)[d] | 1/6 (16.7%)[c,d] | 1/6 (16.7%)[c,d] |
| T2 & T3 | 0/16 (0%)[d] | 2/16 (12.5%)[d] | 1/14 (7.1%)[d] | 1/14 (7.1%)[d] |

[a]Virus isolation was attempted from buffy coat cell preparations from samples collected at 9 intervals from Day 119 (challenge) to Day 147 (amniocentesis). A cow was considered viremic if any blood sample was BVDV positive.
[b]Fetal tissues were collected following abortion or caesarian section. A fetus was considered BVDV positive if any tissues were positive.
[c]One T1 cow, and two T3 cows were eliminated from the study because they were not pregnant at the time of caesarian section and abortions were not observed.
[d]Statistically significant difference vs. placebo group (T1), P ≤ 0.0001

TABLE 5

Maternal serum neutralization (SN) titers and results of challenge in cases where bovine viral diarrhea virus (BVDV) was isolated from vaccinated cows or their fetuses

| Test group | Cow no. | Source of virus isolation | Termination of pregnancy | BVDV1 | BVDV2 |
|---|---|---|---|---|---|
| T3 | 27 | AF | Abortion | 512 | 91 |
| T3 | 60 | AF, FT, IHC | Caesarian section | 181 | 152 |
| T3 | Group GMT | N/A | N/A | 570 | 262 |

AF = amniotic fluid;
FT = fetal tissue;
IHC = immunohistochemistry of fetal tissue;
GMT = geometric mean titer;
NA = not applicable

EXAMPLE 2

Materials and Methods

Animals—Fifty-nine BVDV seronegative (i.e., having serum neutralization [SN] titers<1:2) cows and heifers of breeding age and soundness were obtained from multiple sources and maintained in isolation at research facilities in Nebraska for the duration of the study. Each animal was identified with duplicate ear tags, one placed in each ear. New tags were installed in cases where an animal lost an ear tag. Prior to the study, test animals were inoculated with commercial vaccines for leptospirosis, campylobacteriosis (vibriosis), and clostridial infections. Test animals were maintained under supervision of an attending veterinarian, who clinically monitored them on a daily basis.

Test vaccine—The test vaccine was a multivalent, modified live infectious bovine rhinotracheitis (IBR)-parainfluenza 3 (PI3)-respiratory syncytial virus (RSV) vaccine in desiccated form, rehydrated with an inactivated, liquid BVDV vaccine (CattleMaster/PregSure 5, Pfizer Inc, New York, N.Y.). The BVDV component was combined with a sterile adjuvant. Potency of the BVDV immunizing antigen was established by calculating the geometric mean titer (GMT) for 8 replicate titrations of the bulk fluid used for vaccine preparation. Following rehydration, the IBR-PI3-BRSV-BVDV vaccine was administered in 2 mL doses by either intramuscular (IM) or subcutaneous (SC) injection. The desiccated IBR-PI3-RSV vaccine reconstituted with sterile water was used as a placebo.

Challenge virus—A noncytopathic BVDV type 1 field isolate (Strain 816317, obtained from Dr. E. J. Dubovi, New York State College of Veterinary Medicine, Cornell University) was used as a challenge agent. Virus identity was confirmed by SN and reverse transcriptase polymerase chain reaction (RT-PCR). The RT-PCR analysis was positive for BVDV type 1 nucleotide sequences for the gp53 and p80 proteins and the 5 untranslated region, and negative for the BVDV type 2 p125 sequence. Challenge virus potency was established at a GMT of $10^{4.3}$ TCID$_{50}$ per mL by 2 replicate titrations made immediately before and after challenge. Challenge inoculum was given intranasally in a 4 mL divided dose, 2 mL per nostril.

Serologic assays—Serum neutralization titers for BVDV types 1 and 2 were determined by a constant-virus, decreasing-serum assay in bovine cell culture. Serial dilutions of serum were combined with either 50-300 TCID$_{50}$ of cytopathic BVDV type 1 strain 5960, or a similar amount of cytopathic BVDV type 2 strain 125c.

Virus isolation—Postchallenge isolation of BVDV in bovine cell culture was attempted from peripheral cow blood, amniotic fluid, and fetal tissues. A BVDV-positive cell culture was determined by indirect immunofluorescence using goat anti-BVDV polyclonal antibodies. Isolation of BVDV from fetal tissues was also attempted using immunohistochemistry methods previously described. Haines D M, Clark E G, and Dubovi E J. Vet Pathol 1992; 29:27-32. Whole blood from cows was drawn from the jugular vein in 5-10 mL samples and placed in heparin-containing tubes for preparation of buffy coat cells used for virus isolation attempts. Amniotic fluid was collected under local anesthesia by left-flank laparotomy and aspiration of a 3-5 mL sample from the uterus. Following caesarian section or spontaneous abortion, the eyes, 3 brain sections, spleen, and thymus were aseptically collected from each fetus. Supernatant from homogenized fetal tissues was used for virus isolation attempts in cell culture. For purposes of immunohistochemistry evaluation, fetal tissues were embedded in paraffin and tested in duplicate using 1:800 and 1:600 ascites dilutions containing anti-BVDV monoclonal antibodies.

Biometric data analysis—To demonstrate protection following challenge, a statistically significant reduction in incidence of maternal and fetal infection had to be demonstrated in vaccinated groups (T2 and T3) versus the placebo control group (T1). A Fisher's exact test was used to compare incidence of cow viremia and BVDV isolation from amniotic fluid, fetal tissue, and fetal tissue immunohistochemistry. Serum neutralization titers were analyzed using a mixed linear model with repeated measures. Least squares means from the analysis of variance were used to calculate a geometric mean titer (GMT), which excluded SN data for cows that were not challenged. A probability value of P≤0.05 was used to determine statistical significance.

Fetal protection study—The 59 test animals were randomly assigned to one of three test groups, an IM placebo group (T1), an IM vaccination group (T2), and a SC vaccination group (T3) as noted in Table 6. Cows were inoculated with either vaccine or placebo on study Day 0 and Day 21. In all cases, the Day 0 inoculation was administered on the left side of the neck, and the Day 21 inoculation was administered on the right side of the neck.

On Day 32, all cows received an IM prostaglandin injection (Lutalyse, Pharmacia & Upjohn, Kalamazoo, Mich.) to synchronize estrus. Cows which displayed estrus were bred by artificial insemination with certified BVDV-negative semen. On Day 96, at approximately 60 days of gestation, the pregnancy status of cows was determined by rectal palpation. On Day 103, 10 cows with confirmed pregnancies were randomly selected from each test group, and relocated to a nearby isolation facility (Midwest Veterinary Services, Oakland, Nebr.). On Day 117, these 30 cows were challenged by intranasal inoculation of virulent BVDV. Blood samples were collected on the day of challenge and at 8 postchallenge intervals, on Days 119, 121, 123, 125, 127, 131, 138, and 145, for purposes of BVDV isolation.

On Day 145 (28 days after challenge), left flank laparotomies were performed and amniotic fluid was extracted from each cow. On Day 295, approximately 7-14 days prior to anticipated calving, test cows were transported to facilities at the University of Nebraska, Department of Veterinary and Biomedical Services, for caesarian section. Immediately prior to surgery, a blood sample was collected from each cow for SN assay. Following caesarian delivery (on Days 298-300), a blood sample was collected from each fetus. Fetuses were then euthanized and tissues were aspectically collected for purposes of BVDV isolation.

In cases where spontaneous abortions occurred, blood samples were taken from the dam when abortion was detected and two weeks later. The paired blood samples and aborted fetuses were submitted for serologic testing of blood samples (University of Nebraska Veterinary Diagnositic Center, Lincoln, Nebr.) virus isolation from fetal tissues, (Pfizer Central Research, Lincoln, Nebr.) and histopathologic evaluation of fetal tissues. (Saskatoon Veterinary Biodiagnostics, Saskatoon, SK, Canada.

Results

Individual SN values for the 30 cows used in the fetal protection test were negative for BVDV types 1 and 2 on Day 0, confirming that these test animals were all immunologically naïve to BVDV challenge at the outset of the study. The GMT values (Tables 7 and 8) indicate that IM (T2 group) and SC (T3 group) vaccination both elicited a serologic response following administration of two doses. All cows in the T2 and T3 groups seroconverted (SN titer≥1:8) to BVDV type 1 and BVDV type 2 following the second vaccine dose. At breeding (Day 34-37), the BVDV type 1 SN titers ranged from 1:27 to 1:2,900, and the BVDV type 2 titers ranged from 1:609 to 1:13,777. After vaccination, GMT values for the SC group were marginally higher versus the IM group at each prechallenge interval, but the differences were not statistically significant. Twenty-eight days after challenge (Day 145), the BVDV type 1 GMT values (Table 7) showed a statistically significant difference favoring the SC vaccinates (T3 group) versus the IM (T2) group.

All cows in the placebo group (T1) remained seronegative for both BVDV types 1 and 2 up to the time of challenge (Day 117), indicating that the study was not compromised by adventitious exposure. Placebo cows responded serologically to challenge, but their GMT responses to BVDV types 1 and 2 on Day 145 were significantly lower than the anemnestic responses achieved by either vaccine group (Tables 7 and 8).

Between the time of amniocentesis (Day 145) and caesarian section (Day 298-300), two cows aborted, one from the T1 group and the other from the T3 group. In addition, 4 bred cows (2 T1 placebo cows and one cow each from the T2 and T3 groups) were found to be not pregnant at the time of caesarian section. These 4 cows were confirmed pregnant by rectal palpation on Day 96, approximately 60 days after breeding, indicating that unobserved abortion or fetal resorption occurred. Because fetal tissues from the 4 cows with failed pregnancies were not available for evaluation, these animals were removed from the study. Thus, at the conclusion of the study, 24 of the 30 cows that had been challenged underwent caesarian section, and a total of 26 fetuses resulting from either caesarian delivery or abortion were evaluated for BVDV isolation (Table 6).

Cow number 1317 from the T1 placebo group aborted its fetus on Day 238 (after 201 days of gestation, and 121 days after challenge). Histopathologic and bacteriologic evaluation of the fetus revealed pneumonia, necrosis of the chorionic epithelium, and *Corynebacterium* sp. isolated from the stomach and placenta. Paired serologic samples from the cow did not support IBR, BVD, or leptospirosis as the abortion etiology. Positive BVDV isolation results in cell culture were obtained for peripheral cow blood collected at 6, 8, and 10 days after challenge; for amniotic fluid; and for fetal brain, eye, and thymus, but not the spleen. Fetal brain, eye, thymus, and spleen were immunohistochemistry positive for BVDV. Virus isolation and serologic evidence in this case indicates that a BVDV infected fetus was aborted by a dam that experienced viremia as a result of challenge.

Cow number 1331 from the T3 vaccine group aborted its fetus on Day 249 (after 212 days of gestation, and 132 days after challenge). Histopathologic and bacteriologic evaluation of the fetus revealed a diffuse purulent pneumonia. Cultures of stomach contents and lung were heavily overgrown with coliform bacteria. Paired post-abortion serologic samples from the cow did not support IBR, BVD, or leptospirosis as the abortion etiology. Attempts at BVDV isolation in cell culture were negative for cow peripheral blood collected at all 9 postchallenge intervals, and for amniotic fluid, and fetal brain, eye, spleen and thymus. Immunohistochemistry results for the fetal tissues were negative. However, pooled fetal tissues were positive for BVDV isolation in cell culture. The conflicting results suggest the possibility of contamination of fetal tissues either by contact with pasture seeded with BVD challenge virus or by fomites at the necropsy facility, where BVDV had been previously isolated. The absence of postchallenge viremia in the dam, its positive seroconversion status, and negative BVDV isolation results for specific fetal organs support the conclusion that this fetus was not BVDV infected as a result of challenge. Blood samples collected from each caesarian derived fetus were assayed for SN titers to BVDV type 1 and 2. None of the 7 caesarian derived fetuses from T1 placebo cows was seropositive for either BVDV type 1 or 2. Five of the 17 caesarian derived fetuses from T2 and T3 vaccinates were seropositive for BVDV type 1. Four fetuses had type 1 SN titers of either 1:2 or 1:4, and the fetus from T2 cow 1421 had a type 1 SN titer of 1:181 and a type 2 SN titer of 1:512.

Postchallenge virus isolation results are shown in Table 9. Nine of 10 T1 placebo cows experienced BVDV viremia, indicating that a viable challenge occurred. Blood samples from 19 of the 20 T2 and T3 vaccinates were negative for BVDV viremia on each of 8 postchallenge samples. T2 vaccinate 1421 was BVDV positive on Day 123, 6 days after challenge, and delivered a fetus that was seropositive as noted above, but virus-isolation negative. The 5 percent incidence of postchallenge BVDV viremia in T2 and T3 vaccinates was significantly less ($P \leq 0.0001$) than the 90 percent rate in controls.

Fetal tissues from 2 of 18 vaccinates (11.1 percent), T2 cows 1301 and 1335, were positive for BVDV isolation. This compared to BVDV isolation in 8 of 8 (100 percent) fetuses from T1 placebo cows, a statistically significant difference ($P \leq 0.0001$). BVDV isolation results were either BVDV-positive or -negative for all fetal tissues evaluated, with one exception, T1 cow 1317, from which 3 of 4 fetal tissue samples were positive.

Amniotic fluid from 2 of 20 (10 percent) vaccinates was BVDV positive, versus positive results for 10 of 10 (100 percent) of T1 placebo cows, a statistically significant difference ($P \leq 0.0001$). Amniotic fluid samples from T2 vaccinates 1301 and 1335 were positive.

Immunohistochemistry results were BVDV positive for fetal tissues from 2 of 18 (11.1 percent) vaccinates, T2 cows 1301 and 1335. All fetal tissues evaluated from these vaccinated cows were positive. This corresponded to BVDV isolation results for the same two cows when virus isolation was attempted from amniotic fluid and from fetal tissues using cell culture methods. All fetal tissues from 8 of 8 (100 percent) T1 placebo cows were BVDV positive, a significantly higher incidence (10.0001) versus the vaccinates.

Prechallenge serologic status of the three vaccinated cows with positive BVDV isolation results is shown in Table 10. Cows 1301 and 1335, which delivered BVDV-positive fetuses, and cow 1421, which was viremic, all responded immunologically to vaccination.

Sixteen of 18 fetuses (88.9 percent) from vaccinated cows were refractory to a challenge that produced 100 percent fetal infection in nonvaccinated controls. The intranasal challenge not only mimicked the natural route of infection, but at a dosage much greater than what would be expected from field exposure. Challenge potency also exceeded the level that a prior study found would consistently achieve experimental BVDV type 1 viremia and fetal infection. Ficken M, Jeevaraerathnam S, Wan Welch S K, et al: BVDV fetal infections with selected isolates. In: Proceedings of the International Symposium on Bovine Viral Diarrhea Virus, a Fifty-Year Review. Ithaca, N.Y., 1996; 110-112. A noncytopathic challenge strain was used since this is the biotype associated with persistent infection and infection of immunotolerant fetuses. Cortese VS: Bovine virus diarrhea virus and mucosal disease. In: Current Veterinary Therapy 4, Food Animal Practice. Philadelphia, Pa.: WB Saunders, 1999; 286-291.

Serologic data affirmed vaccine antigenicity by both IM and SC routes of administration. All vaccinated cows seroconverted to both BVDV types, and the marked anamnestic response to challenge (Tables 7 and 8) resulted in GMT titers that persisted until the end of the study, 6 months later. The three vaccinated cows linked to positive virus isolation also seroconverted following vaccination (Table 10). Caesarian-derived calves from seropositive cows 1301 and 1335 were positive for BVDV. Virus isolation from seropositive cows or their fetuses suggests humoral antibody may correlate with protection but is not its sole determinant. Cellular or mucosal mechanisms may also be involved.

TABLE 6

Test groups and final pregnancy status of cows in bovine viral diarrhea virus (BVDV) type 1 fetal challenge study

| Group | Treatment | No. cows vaccinated (Days 0, 21) | No. cows challenged (Day 119) | (1) Maternal death[a] | (2) Abortion[b] | (3) Failed pregnancy[c] | (4) Caesarian section | No. fetuses evaluated for BVDV isolation (1 + 2 + 4) |
|---|---|---|---|---|---|---|---|---|
| T1 | Placebo (IM) | 18 | 7 | 1 | 0 | 1 | 5 | 6 |
| T2 | Vaccine (IM) | 18 | 8 | 0 | 4 | 0 | 4 | 8 |
| T3 | Vaccine (SC) | 20 | 8 | 0 | 3 | 2 | 3 | 6 |

IM = intramuscular vaccination;
SC = subcutaneous vaccination
[a]Abortions occurred on Day 238 (T1 cow) and Day 249 (T3 cow).
[b]All cows with failed pregnancies were confirmed pregnant on Day 96, approximately 60 days after breeding.

TABLE 7

Bovine viral diarrhea virus (BVDV) type 1 serological response in cows challenged with BVDV type 1

| Treatment group | No. seropositive cows on day of breeding[a] | Vaccination (Day 0) | Vaccination (Day 21) | Breeding (Days 34-37) | Challenge (Day 117) | Amniocentesis (Day 145) | Caesarian section (Days 298-300) |
|---|---|---|---|---|---|---|---|
| T1 (n = 10) | 0/10 | <2 | <2 | <2 | <2 | 118.0 | 808.2 (n = 9)[d] |
| T2 (n = 10) | 10/10 | <2 | 5.5[b] | 414.1[b] | 177.4[b] | 10,380.1[b] | 2,233.2[b] (n = 10) |
| T3 (n = 10) | 10/10 | <2 | 7.3[b] | 630.2[b] | 281.2[b] | 20,169.2[b,c] | 3,804.6[b] (n = 9)[e] |
| T2 & T3 (n = 20) | 20/20 | <2 | 6.3[b] | 510.8[b] | 223.3[b] | 14,469.2[b] | 2,914.9[b] (n = 19) |

[a]SN titer reciprocal ≥8.
[b]Statistically significant difference vs. placebo group (T1), P ≤ 0.003
[c]Statistically significant difference vs. IM vaccine group (T2), P = 0.0446
[d]One cow aborted on Day 238.
[e]One cow aborted on Day 249.

TABLE 8

Bovine viral diarrhea virus (BVDV) type 2 serological response in cows challenged with BVDV type 1

| Treatment group | No. seropositive cows on day of breeding[a] | Vaccination (Day 0) | Vaccination (Day 21) | Breeding (Days 34-37) | Challenge (Day 117) | Amniocentesis (Day 145) | Caesarian section (Days 298-300) |
|---|---|---|---|---|---|---|---|
| T1 (n = 10) | 0/10 | <1.4 | <1.4 | <1.4 | <1.4 | 48.5 | 604.9 (n = 9)[d] |
| T2 (n = 10) | 10/10 | <1.4 | 7.6[b] | 1,782.9[b] | 174.8[b] | 3,756.0[b] | 1,634.9[b] (n = 10) |
| T3 (n = 10) | 10/10 | <1.4 | 17.7[b,c] | 2,749.6[b] | 309.7[b] | 4,240.4[b] | 1,879.9[b] (n = 9)[e] |
| T2 & T3 (n = 20) | 20/20 | <1.4 | 11.6[b] | 2,214.1[b] | 232.7[b] | 3,990.9[b] | 1,753.1[b] (n = 19) |

[a] SN titer reciprocal ≥8.
[b]Statistically significant difference vs. placebo group (T1), P ≤ 0.02.
[c]Statistically significant difference vs. IM vaccine group (T2), P = 0.0415
[d]One cow aborted on Day 238.
[e]One cow aborted on Day 249.

TABLE 9

Summary of postchallenge cow and fetal bovine viral diarrhea virus (BVDV) isolation results

| Treatment group | Postchallenge virus isolation method and incidence | | | |
|---|---|---|---|---|
| | Viremia in cows[a] | Amniotic fluid virus isolation | Fetal tissue virus isolation[b] | Fetal tissue immunohisto-chemistry[b] |
| T1 Placebo (IM) | 9/10 (90%) | 10/10 (100%) | 8/8 (100%)[c] | 8/8 (100%)[c] |
| T2 Vaccine (IM) | 1/10 (10%)[d] | 2/10 (20%)[d] | 2/9 (22.2%)[c,d] | 2/9 (22.2%)[c,d] |
| T3 Vaccine (SC) | 0/10 (0%)[d] | 0/10 (0%)[d] | 0/9 (0%)[d] | 0/9 (0%)[c,d] |
| T2 & T3 | 1/20 (5%)[d] | 2/20 (10%)[d] | 2/18 (11.1%)[d] | 2/18 (11.1%)[d] |

[a]Virus isolation was attempted from buffy coat cell preparations from samples collected at 9 intervals from day of challenge (Day 117) to Day 145. A cow was considered viremic if any blood sample was BVDV positive.
[b]Fetal tissues were collected following abortion or caesarian section. A fetus was considered BVDV positive if any tissues were positive.
[c]Two T1 group cows, one T2 group cow, and one T3 group cow were eliminated from the study because they were not pregnant at the time of caesarian section and abortions were not observed.
[d]Statistically significant difference vs. placebo group (T1), P ≤ 0.008.

TABLE 10

Cow pre-challenge serum neutralization (SN) titers in cases where bovine viral diarrhea virus (BVDV) was isolated from vaccinated cows or their fetuses

| Test group | Cow no. | Source of virus isolation | BVDV serotype and reciprocal SN titer at challenge | |
|---|---|---|---|---|
| | | | BVDV1 | BVDV2 |
| T2 | 1301 | FT, AF, IHC | 128 | 181 |
| T2 | 1335 | FT, AF, IHC | 109 | 91 |
| T2 | 1421 | CV | 64[a] | 27[a] |
| T2 | Group GMT | N/A | 177.4 | 174.8 |

FT = fetal tissue;
AF = amniotic fluid;
IHC = immunohistochemistry of fetal tissue;
CV = cow viremia;
NA = not applicable;
GMT = geometric mean titer

EXAMPLE 3

Two groups of 16 cattle were vaccinated twice subcutaneously at an interval of 3 weeks with 2 mL of L. hardjo/L. pomona combination vaccines prepared from two adjuvant formulations: 1) 2.5% Amphigen with Quil A/cholesterol each at 250 mcg/mL, and 2) Amphigen/Al-gel. The vaccines consisted of killed leptospires from which the culture fluids had been removed, so free endotoxin was low. Body temperatures, injection-site reactions, and general health observations were recorded following both injections. No systemic affects were seen, and local reactions were minimal and judged to be clinically acceptable. Sixteen additional cattle were injected with saline as controls. Four weeks after vaccination, cattle were challenged by ocular and vaginal instillation of 5×10$^6$ leptospires on 3 consecutive days. Half of each treatment group was challenged with serovar hardjo and half with pomona. Two pomona controls were eliminated from the study for unrelated reasons, leaving 6 animals in that group. Urine collected weekly, and kidney samples collected at necropsy, 8 weeks after challenge, were evaluated by culture, PCR, and fluorescent antibody microscopy (FA).

Following L. hardjo challenge, viable organisms were detected in urine and/or kidney cultures from 100% (8/8) of the unvaccinated controls, whereas positive cultures were never obtained from any vaccinated animal (0/16). After challenge with L. pomona, 67% (4/6) of the unvaccinated controls became infected on the basis of urine/kidney culture, but none of the vaccinates was ever kidney or urine culture positive (0/16).

Since leptospirosis is transmitted via contaminated urine, the ability to prevent or reduce urinary shedding is a useful measure of vaccine efficacy. Both vaccine formulations reduced urinary shedding of leptospires by statistically significant amounts compared to controls. The data show a substantial benefit from vaccination with the bivalent L. hardjo/L. pomona vaccines formulated with either adjuvant; demonstrating the protection of cattle from infection with leptospires by vaccinating with formalin-killed combination bacterins.

EXAMPLE 4

Materials and Methods

Animals—Thirty-six BVDV and Leptospira seronegative (i.e., having BVDV serum neutralization [SN] titers<1:2 and Leptospira serovars hardjo and pomona [MAT] titers<1:20)) approximately 7-month old calves were obtained from multiple sources and maintained in isolation at research facilities in Nebraska for the duration of the study. Each animal was identified with duplicate ear tags, one placed in each ear. New tags were installed in cases where an animal lost an ear tag. Prior to the study, test animals were vaccinated against clostridial diseases and bovine respiratory disease agents (excluding BVD virus). Test animals were maintained under supervision of an attending veterinarian, who clinically monitored them on a daily basis.

Test vaccines—The experimental test vaccines were liquid vaccines containing either formalin inactivated L. hardjo-bovis or L. pomona, or both, and inactivated BVD type 1 and type 2 viruses. The BVDV components were combined with a sterile adjuvant. Potency of the BVDV immunizing antigens was established by calculating the geometric mean titer (GMT) for 8 replicate titrations of the bulk fluid used for vaccine preparation. Potency of the Leptospira immunizing antigens was established in accordance with a hamster lethality model procedure. The adjuvants in the experimental test vaccines were comprised of either 2.5% Amphigen (v/v) with Quil A/cholesterol each at 100 mcg/ml, with or without 2% (v/v) aluminum hydroxide; 2.5% Amphigen (v/v) with Quil A/Dimethyl dioctadecylammonium bromide (DDA) each at 100 mcg/ml, with or without 2% (v/v) aluminum hydroxide. The experimental test vaccines were administered in 5 mL dose by subcutaneous (SC) injection. A monovalent L. hardjo-bovis bacterin was used as a positive control per manufacturer's instructions. A placebo vaccine containing physiological saline was used as a negative control.

Challenge bacteria—*Leptospira borgpetersenii* serovar hardjo type hardjo-bovis strain 203 (National Animal Disease Center, Ames, Iowa), was used as the challenge agent. *L. hardjo-bovis* challenge material was prepared as first passage organisms which had been isolated from the urine of cattle experimentally infected with *L. hardjo-bovis*. The challenge material was administered once daily for three consecutive days. Each challenge day, a total of two mL of challenge material, containing approximately $2.5 \times 10^6$ *L. hardjo-bovis* organisms/mL, was administered across three separate anatomical sites. The route of challenge was instillation into the conjunctival sac of each eye (½ mL each) and into the vagina (1 mL).

Serologic assays—Serum neutralization titers for BVDV types 1 and 2 were determined by a constant-virus, decreasing-serum assay in bovine cell culture. Serial dilutions of serum were combined with either 50-300 TCID$_{50}$ of cytopathic BVDV type 1 strain 5960, or a similar amount of cytopathic BVDV type 2 strain 125c. Serum microscopic agglutination titers (MAT) for *L. hardjo-bovis* and *L. pomona* were conducted using a standard test at a qualified veterinary diagnostic center (Cornell University College of Veterinary Medicine Diagnostic Laboratory).

*Leptospira* isolation—Urine samples and kidney tissue homogenates (pooled left and right kidney) were examined for the presence of Leptospira. Urine and kidney cultures were examined for *Leptospira* once weekly for up to 8 weeks using standard procedures. *Leptospira* fluorescent antibody (FA) techniques were conducted using a standard test at a qualified veterinary diagnostic center (Cornell University College of Veterinary medicine Diagnostic Laboratory.

Biometric data analysis—To demonstrate protection following challenge, a statistically significant reduction in incidence of *Leptospira* infection had to be demonstrated in vaccinated groups (Table 11) (T02, T03, T04 and T05) versus the placebo control group (T1). Data for kidney colonization and urinary shedding were summarized by treatment and timepoint. Comparisons between treatments were made as to the percent of animals with *Leptospira* detected in the kidney. Comparisons between treatments were made as to the percent of animals with *Leptospira* detected in the urine. A Fisher's Exact test was used for the analyses above. Duration of *Leptospira* shedding in the urine was also compared using a general linear mixed model. A probability value of P≤1.05 was used to determine statistical significance.

*Leptospira* protection study—The 36 test animals were randomly assigned to one of six test groups as indicated in Table 11. On Day 0 and Day 21, each animal assigned to T01-T05 received one 5 mL SC dose of the appropriate experimental test or placebo vaccine. On Day 0 and Day 28, each animal assigned to T06 received one 2 mL SC dose of the positive control vaccine. On Days 57-59, all animals were challenged with *L. hardjo-bovis* strain 203 as outlined above.

Blood samples were collected from each animal on Days 0, 21, 35, 56, 84, and 111 for determination of BVDV type 1 and type 2 titers.

Urine samples (approximately 45 mL) were collected from each animal on Days −1, 56, 70, 77, 84, 91, 98 and 105 for leptospire isolation as described above.

Animals were euthanized on Days 112 and 113 and kidneys evaluated for the presence of leptospires as described above.

Results

The GMT values (Table 12) indicate that all the animals receiving BVDV-Leptopsira combination vaccines (T02, T03, T04 and T05) elicited a serologic response following administration of two vaccine doses. All the animals in groups T02, T03, T04 and T05 seroconverted (SN titer≥1:8) to BVDV type 1 following the second vaccine dose. All the animals in groups T02, T04 and T05 seroconverted (SN titer≥1:8) to BVDV type 2 following the second vaccine dose. All cows in the placebo group (T01) or in the group that received monovalent *L. hardjo-bovis* vaccine remained seronegative from both BVDV types 1 and 2, indicating that the study was not compromised by adventitious exposure. Collectively, the BVDV serology data shows for the first time that combination vaccines comprising inactivated BVDV types 1 and 2 and inactivated *L. hardjobovis* and *L. pomona* formulated in four different adjuvants can induce a protective response against BVDV disease in cattle, since a cow BVDV SN titer of ≥1:8 is known in the art to be indicative of protection against BVDV disease.

The *Leptospira* urine and kidney results (Table 13) indicate that all animals that received BVDV-Leptospira combination vaccines (T02, T03, T04 and T05) were urine culture (CX) negative (Table 13, column 2) at all eight timepoints tested and kidney culture negative (Table 13, column 8) at necropsy (Day 112 or 113). Cows that received *Leptospira* monovalent vaccine (T06, positive control) were similarly protected against *Leptospira* infection. In contrast, cows that received placebo vaccine (T01, negative control) were infected based on urine (Table 13, column 2) and kidney culture (Table 13, column 8), indicating the vaccine challenge study was valid. Collectively, the *L. hardjobovis* isolation data shows for the first time that combination vaccines comprising inactivated BVDV types 1 and 2 and inactivated *L. hardjobovis* and *L. Pomona* formulated in four different adjuvants can induce a protective response against *Leptospira* disease in cattle.

TABLE 11

Test groups of calves in BVDV-*Leptospira* combination vaccine study

| Treatment | Vaccine | Number of Animals | Dose Volume | Route of Administration | Number of Doses/Animal | Dosing Interval |
|---|---|---|---|---|---|---|
| T01 | Saline placebo | 6 | 5 mL | SC | 2 | 3 weeks |
| T02 | L. hardjobovis-L. Pomona-BVDV-1-BVDV-2 in QAC | 6 | 5 mL | SC | 2 | 3 weeks |
| T03 | L. hardjobovis-L. Pomona-BVDV-1-BVDV-2 in QAC/AIOH | 6 | 5 mL | SC | 2 | 3 weeks |

TABLE 11-continued

Test groups of calves in BVDV-*Leptospira* combination vaccine study

| Treatment | Vaccine | Number of Animals | Dose Volume | Route of Administration | Number of Doses/Animal | Dosing Interval |
|---|---|---|---|---|---|---|
| T04 | L. hardjobovis-L. Pomona-BVDV-1-BVDV-2 in DDA | 6 | 5 mL | SC | 2 | 3 weeks |
| T05 | L. hardjobovis-L. Pomona-BVDV-1-BVDV-2 in DDA/AlOH | 6 | 5 mL | SC | 2 | 3 weeks |
| T06 | L. hardjobovis monovalent | 6 | 2 mL | SC | 2 | 4 weeks |

TABLE 12

BVDV Types 1 and 2 Serum Neutralization Reciprocal Geometric Mean Titers and Ranges (#-#) on Day 35
Serum Virus Neutralization Reciprocal Geometric Mean Titer and Range (#-#) on Day 35

| Treatment | BVD Virus Type 1 | BVD Virus Type 2 |
|---|---|---|
| T01 | <2 (<2-<2) | <2 (<2-<2) |
| T02 | 1084.9 (609-2435) | 20.8 (16-54) |
| T03 | 148.0 (<2-1218) | 5.8 (<2-19) |
| T04 | 1877.9 (1024-2896) | 34.0 (19-91) |
| T05 | 1084.6 (152-3444) | 36.1 (10-91) |
| T06 | <2 (<2-<2) | <2 (<2-<2) |

TABLE 13

Efficacy Results of BVDV-*Leptospira* Combination Vaccines Against *Leptospira* hardjo-bovis Challenge

| Treatment | Percent of Calves Ever Positive for Leptospira in Urine | | | Least Squares Mean Percent Days of Leptospira Positive Urine | | | Percent of Calves Ever Positive for Leptospira in Kidneys | | |
|---|---|---|---|---|---|---|---|---|---|
| | CX | FA | PCR | CX | FA | PCR | CX | FA | PCR |
| T01 n = 6 | 100$^a$ | 83.3$^a$ | 83.3$^a$ | 50.9$^a$ | 29.1$^a$ | 37.1$^a$ | 83.3$^a$ | 0$^a$ | 16.7$^a$ |
| T02 n = 6 | 0$^b$ | 0$^b$ | 0$^b$ | 0$^b$ | 0$^b$ | 0$^b$ | 0$^b$ | 0$^a$ | 0$^a$ |
| T03 n = 6 | 0$^b$ | 0$^b$ | 0$^b$ | 0$^b$ | 0$^b$ | 0$^b$ | 0$^b$ | 50.0$^a$ | 0$^a$ |
| T04 n = 6 | 0$^b$ | 0$^b$ | 0$^b$ | 0$^b$ | 0$^b$ | 0$^b$ | 0$^b$ | 0$^a$ | 0$^a$ |
| T05 n = 6 | 0$^b$ | 16.7$^{ab}$ | 16.7$^{ab}$ | 0$^b$ | 0.3$^b$ | 0.4$^b$ | 0$^b$ | 16.7$^a$ | 0$^a$ |
| T06 n = 6 | 0$^b$ | 0$^b$ | 33.3$^{ab}$ | 0$^b$ | 0$^b$ | 1.6$^b$ | 0$^b$ | 0$^a$ | 0$^a$ |

Values within a column not sharing a common superscript were significantly (P < 0.05) different

EXAMPLE 5

Materials and Methods

Animals—Twenty BVDV seronegative (i.e., having serum neutralization [SN] titers<1:2) cows were obtained and maintained in research isolation facilities for the duration of the study. Each animal was identified with duplicate ear tags, one placed in each ear. New tags were installed in cases where an animal lost an ear tag. Test animals were maintained under supervision of an attending veterinarian, who clinically monitored them on a daily basis.

Test vaccine—The test vaccine was a multivalent, modified live infectious bovine rhinotracheitis (IBR)-parainfluenza 3 (PI3)-respiratory syncytial virus (RSV) vaccine in desiccated form, rehydrated with an inactivated, liquid 8-way BVDV-*Leptospira* spp-*Campylobacter fetus* containing vaccine in a Quil A/cholesterol/Amphigen adjuvant. (Pfizer Inc, New York, N.Y.) The liquid composition consisted of inactivated BVDV-1 and -2 viruses, five inactivated *Leptospira* species (*L. canicola, L. grippotyphosa, L. borgpetersenii hardjo-prajitno, L. icterohaemorrhagiae* and *L. interrogans pomona*) and inactivated *C. fetus* bacterin combined with a Quil A/cholesterol/Amphigen adjuvant sterile adjuvant. Control vaccine consisted of the five inactivated *Leptospira* spp. described above and inactivated *C. fetus* bacterin combined with a sterile mineral oil (Drakeol) adjuvant. Test vaccine was given by subcutaneous injection and control vaccine was given by intramuscular injections. Vaccines were administered on Day 0 on the right side of the neck and on Day 21 on the left side of the neck.

Challenge virus—A cytopathic BVDV type 2 field isolate (Strain 24515) was used as a challenge agent. Challenge virus potency was established at a GMT of $10^{5.4}$ TCID$_{50}$/5 mL by 2 replicate titrations made immediately before and after challenge. Challenge inoculum was given intranasally on Day 42 in a 5 mL divided dose, approximately 2.5 mLs per nostril.

Serologic assays—Serum neutralization titers for BVDV types 1 and 2, BHV-1, PI3 and BRSV were determined by a constant-virus, decreasing-serum assay in bovine cell culture using standard procedures. *C. fetus* antibody titers were determined by a standard agglutination assay.

Virus isolation—Postchallenge (PC) isolation of BVDV in bovine cell culture was conducted from peripheral white blood cells (buffy coats) on Days 42 and 45-52. A BVDV-positive cell culture was determined by indirect immunofluorescence using goat anti-BVDV polyclonal antibodies. Whole blood from cows was drawn from the jugular vein in 5-10 mL samples and placed in heparin-containing tubes for preparation of buffy coat cells used for virus isolation attempts.

Clinical Disease Scoring—Each animal was scored on Days 40-56 post-challenge. A normal animal with no clinical signs received a score of zero. An animal with nonspecific clinical signs (eg nasal discharge, abnormal respiration, and lethargy) not specific for acute BVD virus infection received a score of one. A score of two was assigned to any animal with acute BVD clinical disease in which clinical signs as a whole were moderate and specific for acute BVD virus infection. Clinical signs include nasal discharge, abnormal respiration, lethargy, gauntness, ocular discharge, hypersalivation, diarrhea, dehydration, lameness and/or reluctance to move. An animal with clinical signs that as a whole were severe in degree was assigned a score of three.

Biometric data analysis—For serum virus neutralization, titers were transformed to log base 2 and analyzed by a mixed linear model with repeated measures. Backtransformation was done to calculate geometric mean titer (GMT). Percent number of days with positive virus isolation was analyzed using a mixed linear model. Pairwise comparison of test versus control vaccine groups were made. A probability value of $P \leq 0.05$ was used to determine statistical significance.

Results

No adverse events were observed during or immediately following administration of the 2 vaccine doses.

All cows were seronegative to BVDV types 1 and 2 and BHV-1 prior to vaccination (Day 0), confirming that the test animals were immunologically naïve to BVDV and BHV-1 at the outset of the study. The GMT values for all five viral fractions on Day 0 and Day 35 (14 days post-second vaccination) are shown in Table 14.

Results show that the 11-way test vaccine composition was immunogenic in cattle since differences in antibody titers to all 5 viruses were observed between pre-vaccination (Day 0) and post-vaccination (Day 35) timepoints. In addition, post-vaccination (Day 35) titers to C. fetus were similar between the 5-way control and 11-way test vaccine, demonstrating that the presence of the modified-live and killed viral fractions in the 11-way vaccine did not interfere with ability of the host to mount an immune response against the C. fetus bacterial fraction.

EXAMPLE 6

Materials and Methods

Animals—Thirty male and female calves were selected for the study from a single herd. The ages of these calves were estimated to be 6 to 8 months based on their body weights on Day 0. An additional ten calves from the same herd [six were not] were enrolled on Day 18; however, they had not been weighed. Prior to being enrolled in the study (Day 0 for T02, T03, T04, and Day 18 for T01) all animals were seronegative (SVN<1:2) for antibodies to BVD virus Type 1 and Type 2. Each animal was identified with duplicate ear tags, one placed in each ear. New tags were installed in cases where an animal lost an ear tag. Test animals were maintained under supervision of an attending veterinarian, who clinically monitored them on a daily basis.

Test vaccine—The test vaccines were prepared by reconstituting the lyophilized modified live virus vaccine Cattle-Master™, containing modified live infectious bovine rhinotracheitis (IBR)-parainfluenza 3 (PI3)-respiratory syncytial virus (RSV) with one of the killed BVD liquid diluents (containing BVDV types 1 and 2) prepared in a microfluidized saponin-based (Quil A or GPI-0100) oil-in-water emulsion. The method for preparation of a microfluidized saponin-based oil-in-water emulsion is described in Application Ser. No. 60/460,301, filed Apr. 4, 2003, incorporated herein by reference. (Treatment groups are shown in Table 15).

TABLE 14

Serum viral neutralization titers to BVDV type 1, BVDV type 2, BHV-1, PI3 and BRSV and agglutination antibody titers to C. fetus prior to (Day 0) and following vaccine administration.

| | Vaccine | BVDV-1 | | BVDV-2 | | BHV-1 | | PI3 | | BRSV | | C. fetus | |
|---|---|---|---|---|---|---|---|---|---|---|---|---|---|
| Vaccine | Components | 0 | 35 | 0 | 35 | 0 | 35 | 0 | 35 | 0 | 35 | 0 | 35 |
| Control | 5 Leptospira spp., C. fetus | 1 | 1[a] | 1 | 1[a] | 1 | 1[a] | 140 | 175 | 8 | 14 | 57 | 260 |
| Test | BHV-1, PI3 BRSV, BVDV-1 BVDV-2 5 Leptospira spp., C. fetus | 1 | 8[b] | 1 | 18[b] | 1 | 145[b] | 155 | 453 | 16 | 57 | 26 | 422 |

[a,b]Significant differences between vaccine treatments within a column are indicated by different subscripts

TABLE 15

Treatment Groups used in Saponin-based Oil-in-Water Emulsion Vaccine Efficacy Study

| Group | # of calves | Vaccine Fractions | Saponin Adjuvant | # of Doses |
|---|---|---|---|---|
| T01 | 10 | 0.9% saline | none | 2 |
| T02 | 10 | Modified-live BHV-1<br>Modified-live PI3<br>Modified-live BRSV<br>Killed BVDV 1<br>Killed BVDV 2 | Quil A<br>0.5 mg/dose | 2 |
| T03 | 5 | Modified-live BHV-1<br>Modified-live PI3<br>Modified-live BRSV<br>Killed BVDV 1<br>Killed BVDV 2 | GPI-0100<br>0.5 mg/dose | 2 |
| T03 | 15 | Modified-live BHV-1<br>Modified-live PI3<br>Modified-live BRSV<br>Killed BVDV 1<br>Killed BVDV 2 | GPI-0100<br>1.0 mg/dose | 2 |

Vaccines were administered as a single 2 mL dose subcutaneously (SC) on the right side of the neck for the first administration (Day 0 and/or Day 2) and on the left side of the neck for the second administration (Day 21). Injections were administered in the lateral neck approximately midway between the scapula and the poll.

Challenge virus—The challenge virus was non-cytopathic Bovine Viral Diarrhea virus (BVDV) Type 2, strain 24515. On Day 42 a 5 mL dose of the challenge virus preparation (approximately 2.5 mL per nostril) was administered intranasally (needle-less syringe administration) to animals in treatments T01, T02, T03 and T04. The challenge material was titrated for virus content (two replicates per assay) prior to and following challenge administration. The mean titers pre-challenge and post-challenge were 5.5 $\log_{10}$ and 5.3 $\log_{10}$ per 5 mL dose, respectively.

Serologic assays—Blood samples (two 13 mL SST tubes) for BVD serology were collected o Days 0, 21, 35, 43, and 57. Serum neutralization titers for BVDV types 1 and 2, BHV-1, were determined by a constant-virus, decreasing-serum assay in bovine cell culture using standard procedures.

Total White Blood Cell (WBC) Counts: Blood samples (One 4 mL EDTA tube) for total WBC determination were collected from T01-T04 animals on Days 41, 42 and 43 (prior to challenge and following challenge) and on Days 44 through 57. Blood samples were processed and transferred to Physicians Laboratory Services, Inc. for analysis. The results were transferred electronically into a Clinical Data Management System Virus isolation—Blood samples (one 8 mL CPT tube) for BVD virus isolation were collected from T01-T04 on Day 43 (prior to challenge) and on Days 44-57. A BVDV-positive cell culture was determined by indirect immunofluorescence using goat anti-BVDV polyclonal antibodies Clinical Disease Scoring—Clinical disease scores of 0, 1, 2, or 3 based on clinical signs attributable to BVD 2 infection (see above, example 4), were made for each animal T01-T04 on Days 41 through 43 (prior to challenge) and Days 44 through 57.

Biometric data analysis—For serum virus neutralization, titers were transformed to log base 2 and analyzed by a mixed linear model with repeated measures. Backtransformation was done to calculate geometric mean titer (GMT). Percent number of days with positive virus isolation was analyzed using a mixed linear model. Pairwise comparison of test versus control vaccine groups were made. A probability value of $P \leq 0.05$ was used to determine a statistical significance.

Results

No untoward systemic reactions were observed in any of the animals during the vaccination phase of the study (Days 0 through 42).

The geometric mean reciprocal SVN titers for antibodies to the BVD virus Type 1 and Type 2 are summarized in Tables 16 and 17.

TABLE 16

Geometric Mean SVN Titers for Antibodies to BVD Virus Type 1

| | | BVD-1 Geometric Mean Reciprocal SVN Titers on Study Day | | | | |
|---|---|---|---|---|---|---|
| Treatment | N | 0 | 21 | 35 | 43[1] | 57 |
| T01 saline | 10 | NS[1] | <2[b] | <2[b] | <2[b] | 43.6[b] |
| T02 Quil A, 0.5 mg | 10 | <2 | 12.5[a] | 2393.6[a] | 2797.9[a] | 31651.6[a] |
| T03 GPI, 0.5 mg | 5 | <2 | 22.1[a,c] | 8480.8[c] | 7912.9[c] | 92682.0[a] |
| T04 GPI, 1.0 mg | 15 | <2 | 24.6[a,c] | 6968.7[c] | 6136.9[c] | 61857.7[a] |

TABLE 17

Geometric Mean SVN Titers for Antibodies to BVD Virus Type 2

| | | BVD-2 Geometric Mean Reciprocal SVN Titers on Study Day | | | | |
|---|---|---|---|---|---|---|
| Treatment | N | 0 | 21 | 35 | 43[2] | 57 |
| T01 saline | 10 | NS[1] | <2[b] | <2[b] | <2[b] | 494.6[b] |
| T02 Quil A, 0.5 mg | 10 | <2 | 4.0[a] | 469.4[a] | 587.1[a] | 75281.2[a] |
| T03 GPI, 0.5 mg | 5 | <2 | <2[b] | 100.3[c] | 87.4[c] | 18820.1[c] |
| T04 GPI, 1.0 mg | 15 | <2 | <2[b] | 125.5[b] | 100.1[c] | 18604.0[c] |

Values for each day either with no superscripts or the same superscript were not statistically significant, $P \geq 0.05$
NS = Animals not on study As shown in Tables 16 and 17, all three saponin containing oil-in water emulsion adjuvants induced statistically significant antibody titers to BVDV type 1 and type 2 viruses on Days 21, 35, 43, and 57. Collectively, these data demonstrate that vaccine compositions comprising modified-live BHV-1, PI3, BRSV and at least one additional antigen and an adjuvant that comprises a saponin containing oil-in-water emulsion is immunogenic in cattle. In addition, these data demonstrate such vaccines comprising saponin containing oil-in-water microfluidized emulsion as the adjuvant are immunogenic in cattle.

What is claimed is:

1. A method of preventing abortion caused by Bovine Herpes Virus (BHV-1) in a cow comprising administering to said cow or heifer a therapeutically effective amount of a vaccine composition comprising:
    a modified live Bovine Herpes Virus (BHV-1);
    a modified live parainfluenza virus Type 3 (PI3);
    a modified live Bovine Respiratory Syncytial Virus (BRSV);
    a Bovine Viral Diarrhea Virus Type-1 (BVDV-1);
    a Bovine Viral Diarrhea Virus Type-2 (BVDV-2);
    an adjuvant; and
    a veterinarily-acceptable carrier, wherein said cow is a pregnant cow or a lactating cow.

2. The method of claim 1, wherein said cow is the lactating cow.

3. The method of claim 1, wherein said cow is the pregnant cow.

4. The method of claim 1, wherein said vaccine contains from about $10^3$ to about $10^{10}$ colony forming units per dose of each virus.

5. The method of claim 1, wherein the amount of said vaccine administered is from about 0.5 to about 5.0 ml per dose.

6. A method of treating or preventing persistent fetal infection in a cow, comprising administering to said cow or heifer an effective amount of a vaccine composition comprising:
- a modified live Bovine Herpes Virus (BHV-1);
- a modified live parainfluenza virus Type 3 (PI13);
- a modified live Bovine Respiratory Syncytial Virus (BRSV);
- a Bovine Viral Diarrhea Virus Type-1 (BVDV-1);
- a Bovine Viral Diarrhea Virus Type-2 (BVDV-2);
- an adjuvant; and
- a veterinarily-acceptable carrier wherein said cow is a pregnant cow or a lactating cow.

7. The method of claim 6, wherein said cow is the lactating cow.

8. The method of claim 6, wherein said cow is the pregnant cow.

9. The method of claim 6, wherein said vaccine contains from about $10^3$ to about $10^{10}$ colony forming units per dose of each virus.

10. The method of claim 6, wherein the amount of said vaccine administered is from about 0.5 to about 5.0 ml per dose.

11. The method of claim 1, wherein the composition further comprises at least one antigen selected from the group consisting of *Leptospira canicola*, *Leptospira grippotyphosa*, *Leptospira borgpetersenii hardjo-prajitno*, *Leptospira icterohaemmorrhagia*, *Leptospira interrogans pomona*, *Leptospira borgpetersenii hardjo-bovis*, and *Campylobacter fetus*.

12. The method of claim 1, wherein said adjuvant comprises a saponin-containing oil-in-water emulsion.

13. The method of claim 12, wherein said saponin-containing oil-in-water emulsion is microfluidized.

14. The method of claim 1, wherein said adjuvant comprises Quil A, cholesterol, and a lecithin and oil blend.

15. The method of claim 6, wherein the composition further comprises at least one antigen selected from the group consisting of *Leptospira canicola*, *Leptospira grippotyphosa*, *Leptospira borgpetersenii hardjo-projitno*, *Leptospira icterohaemmorrhagia*, *Leptospira interrogans pomona*, *Leptospira borgpetersernii hardjo-bovis*, and *Campylobacter fetus*.

16. The method of claim 6, wherein said adjuvant comprises a saponin-containing oil-in-water emulsion.

17. The method of claim 16, wherein said saponin-contain oil-in-water emulsion is microfluidized.

18. The method of claim 6, wherein said adjuvant comprises Quil A, cholesterol, and a lecithin and oil blend.

\* \* \* \* \*